(12) United States Patent
Marasco et al.

(10) Patent No.: US 10,675,349 B2
(45) Date of Patent: Jun. 9, 2020

(54) HUMANIZED CC CHEMOKINE RECEPTOR 4 (CCR4) ANTIBODIES AND METHODS OF USE THEREOF

(71) Applicant: Dana-Farber Cancer Institute, Inc., Boston, MA (US)

(72) Inventors: Wayne A. Marasco, Wellesley, MA (US); Quan Zhu, Needham, MA (US); De-Kuan Chang, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 8 days.

(21) Appl. No.: 15/517,108

(22) PCT Filed: Oct. 6, 2015

(86) PCT No.: PCT/US2015/054202
§ 371 (c)(1),
(2) Date: Apr. 5, 2017

(87) PCT Pub. No.: WO2016/057488
PCT Pub. Date: Apr. 14, 2016

(65) Prior Publication Data
US 2017/0290911 A1    Oct. 12, 2017

Related U.S. Application Data

(60) Provisional application No. 62/060,381, filed on Oct. 6, 2014.

(51) Int. Cl.
| | | |
|---|---|---|
| *C07K 16/18* | (2006.01) |
| *A61K 39/395* | (2006.01) |
| *C07K 16/28* | (2006.01) |
| *A61K 39/00* | (2006.01) |
| *C07K 16/24* | (2006.01) |

(52) U.S. Cl.
CPC ...... *A61K 39/3955* (2013.01); *A61K 39/0011* (2013.01); *A61K 39/39558* (2013.01); *C07K 16/18* (2013.01); *C07K 16/24* (2013.01); *C07K 16/246* (2013.01); *C07K 16/2809* (2013.01); *C07K 16/2866* (2013.01); *A61K 2039/507* (2013.01); *C07K 2317/31* (2013.01); *C07K 2317/33* (2013.01); *C07K 2317/35* (2013.01); *C07K 2317/52* (2013.01); *C07K 2317/56* (2013.01); *C07K 2317/622* (2013.01); *C07K 2317/76* (2013.01); *C07K 2317/92* (2013.01); *C07K 2319/00* (2013.01); *C07K 2319/01* (2013.01)

(58) Field of Classification Search
CPC .......................... A61K 39/3955; C07K 16/18
USPC ..................................................... 424/133.1
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,522,811 A | 6/1985 | Eppstein et al. |
| 4,544,545 A | 10/1985 | Ryan et al. |
| 4,676,980 A | 6/1987 | Segal et al. |
| 4,816,567 A | 3/1989 | Cabilly et al. |
| 4,946,778 A | 8/1990 | Ladner et al. |
| 5,013,556 A | 5/1991 | Woodle et al. |
| 5,030,719 A | 7/1991 | Umemoto et al. |
| 5,091,513 A | 2/1992 | Huston et al. |
| 5,132,405 A | 7/1992 | Huston et al. |
| 5,223,409 A | 6/1993 | Ladner et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,916,771 A | 6/1999 | Hori et al. |
| 5,939,598 A | 8/1999 | Kucherlapati et al. |
| 2002/0098527 A1 | 7/2002 | Kenya |
| 2007/0172476 A1 | 7/2007 | Ryuzo |

FOREIGN PATENT DOCUMENTS

| | | |
|---|---|---|
| EP | 0586505 | 3/1994 |
| EP | 1330114 | 7/2003 |
| WO | WO 91/00360 | 1/1991 |
| WO | WO 92/000373 | 1/1992 |
| WO | WO 94/02602 | 2/1994 |
| WO | WO 94/011026 | 5/1994 |
| WO | WO 95/22618 | 8/1995 |
| WO | WO 96/34096 | 10/1996 |
| WO | WO 99/53049 | 10/1999 |

(Continued)

OTHER PUBLICATIONS

Fischer et al (Pathobiology, 2007, 74: 3-14).*
Liu et al (Med Oncol, 2014, 31(882): 1-6).*
Stillebroer et al (European Urology, 2010, 58: 75-83).*
Baatar, D., et al. Human peripheral blood T regulatory cells (Tregs), functionally primed CCR4+ Tregs and unprimed CCR4− Tregs, regulate effector T cells using F asL. J Immunol 178, 4891-4900 (2007).
Barbas et al., "Recombinant human Fab fragments neutralize human type 1 immunodeficiency virus in vitro", Proc. Natl. Acad. Sci. USA 89:9339-43 (1992).

(Continued)

*Primary Examiner* — Sean E Aeder
(74) *Attorney, Agent, or Firm* — Baker Donelson

(57) ABSTRACT

The present invention provides humanized monoclonal antibodies, bi-specific antibodies, antibody conjugates, and fusion proteins that bind to the chemokine receptor CCR4. This antibody is derived from CCR4-IgG1 and recognizes the same epitope. This antibody contains either an IgG4 or a stabilized IgG4 in order to improve binding efficiency and reduce in vivo Fab arm exchange. Binding of the antibodies disclosed herein to CCR4 inhibits ligand-mediated activities and is used to treat symptoms of cancer.

25 Claims, 9 Drawing Sheets
Specification includes a Sequence Listing.

(56) References Cited

FOREIGN PATENT DOCUMENTS

| WO | 2009/086514 A1 | 7/2009 |
|---|---|---|
| WO | 2013/166500 A1 | 11/2013 |
| WO | WO 2013/166500 | 11/2013 |

OTHER PUBLICATIONS

Bobo et al., "Convection-enhanced delivery of macromolecules in the brain", Proc. Natl. Acad. Sci. USA 91:2076-2080 (1994).
Brodeur et al., "Monoclonal Antibody Production Techniques and Applications", pp. 51-63 (1987).
Caron et al., "Engineered Humanized Dimeric Forms of IgG Are More Effective Antibodies", J. Exp Med., 176: 1191-1195 (1992).
Carell, et al., "A Novel Procedure for the Synthesis of Libraries Containing Small Organic Molecules", Angew. Chem. Int. Ed. Engl. 33: 2059, (1994).
Cho, et al., "An Unnatural Biopolymer", Science 261: 1303, (1993).
Cole, et al., 1985 In: Monoclonal Antibodies and Cancer Therapy, Alan R. Liss, Inc., pp. 77-96.
Cote, et al., "Generation of human monoclonal antibodies reactive with cellular antigens", Proc Natl Acad Sci USA 80: 2026-2030, (1983).
Cull, et al., "Screening for receptor ligands using large libraries of peptides linked to the C terminus of the lac repressor", Proc. Natl. Acad. Sci. USA 89: 1865-1869 (1992).
Curiel, T.J., et al. Specific recruitment ofregulatory T cells in ovarian carcinoma fosters immune privilege and predicts reduced survival. Nat lvfed 10, 942-949 (2004).
Cwirla, et al., "Peptides on phage: A vast library of peptides for identifying ligands", Proc. Natl. Acad. Sci. U.S.A. 87: 6378-6382, (1990).
Davies et al. "Antibodies-Antigen Complexes", Annual Rev Biochem 59:439-473 (1990).
Davidson, et al., "A model system for in vivo gene transfer into the central nervous system using an adenoviral vector", Nat. Genet 3:219 (1993).
Devlin, "Random Peptide Libraries: A Source of Specific Protein Binding Molecules", Science 249: 404-406 (1990).
DeWitt, et al., ""Diversomers": An approach to nonpeptide, nonoligomeric chemical diversity", Proc. Natl. Acad. Sci. U.S.A. 90: 6909 (1993).
Epstein et al., "Biological activity of liposome-encapsulated murine interferon y is mediated by a cell membrane receptor", Proc. Natl. Acad. Sci. USA, 82: 3688 (1985).
Erb et al., "Recursive deconvolution of combinatorial chemical libraries", Proc. Natl. Acad. Sci. U.S.A. 91: 11422 (1994).
Faget, J., et al. Early detection of tumor cells by innate immune cells leads to T(reg) recruitment through CCL22 production by tumor cells. Cancer Res 71, 6143-6152 (2011).
Felici, "Selection of Antibody Ligands from a Large Library of Oligopeptides Expressed on a Multivalent Exposition Vector", J. Mol. Biol. 222: 301-310, (1991).
Fishwild et al, "High-avidity IgGk monoclonal antibodies from a novel strain of minilocus transgenic mice", Nature Biotechnology 14, 845-51 (1996).
Fodor et al. "Multiplexed biochemical assays with biological chips", Nature 364: 555-556 (1993).
Gallop et al., "Applications of Combinatorial Technologies to Drug Discovery. 1. Background and Peptide Combinatorial Libraries", J. Med. Chem 37: 1233, (1994).
Geller, A. I. et al., "An HSV-1 Vector Expressing Tyrosine Hydroxylase Causes Production and Release of L-DOPA from Cultured Rat Striatal Cells", J. Neurochem, 64:487 (1995).
Geller, A. I. et al., "Long-term increases in neurotransmitter release from neuronal cells expressing a constitutively active adenylate cyclase from a herpes simplex virus type 1 vector", Proc Natl. Acad. Sci.: U.S.A. 90:7603 (1993).

Geller, A. I., et al., "Infection of cultured central nervous system neurons with a defective herpes simplex virus 1 vector results in stable expression of Escherichia coli β-galactosidase", Proc Natl. Acad. Sci USA 87:1149 (1990).
Gobert, M., et al. "Regulatory T cells recruited through CCL22/CCR4 are selectively activated in lymphoid infiltrates smTounding primary breast tumors and lead to an adverse clinical outcome", Cancer Res 69, 2000-2009 (2009).
Goding, "Monoclonal Antibodies: Principles and Practice", Academic Press, pp. 59-103, (1986).
Han, T., et al. "Human Anti-CCR4 Minibody Gene Transfer for the Treatment of Cutaneous T-Cell Lymphoma", PLoS One 7, e44455 (2012).
Hiraoka, N. et al. "Prevalence of FOXP3$^+$ regulatory T cells increases during the progression of pancreatic ductal adenocarcinoma and its premalignant lesions", Clin Cancer Res 12, 5423-5434 (2006).
Hoogenboom and Winter, "By-passing Immunisation Human Antibodies from Synthetic Repertoires of Germline VH Gene Segments Rearranged in Vitro", J. Mol. Biol., 227:381 (1992).
Houghten et al., "The Use of Synthetic Peptide Combinatorial Libraries for the Identification of Bioactive Peptides", Biotechniques 13:412-421 (1992).
Huse, et al., "Generation of a Large Combinatorial Library of the Immunoglobulin Repertoire in Phage Lambda", Science 246: 1275-1281 (1989).
Huston et al."Protein engineering of antibody binding sites: Recovery of specific activity in an anti-digoxin single-chain Fv analogue produced in Escherichia coli", Proc Nat Acad Sci USA 85(16):5879-5883 (1988).
Hwang et al., "Hepatic uptake and degradation of unilamellar sphingomyelin/cholesterol liposomes: A kinetic study", Proc. Natl Acad. Sci. USA, 77: 4030 (1980).
Iellem, A., et al. "Unique chemotactic response profile and specific expression of chemokine receptors CCR4 and CCR8 by CD4$^+$CD25$^+$ regulatory T cells", J Exp Med 194, 847-853 (2001).
Imai, T., et al. "Selective recruitment of CCR4-bearing Th2 cells toward antigenpresenting cells by the CC chemokines thymus and activation-regulated chemokine and macrophage-derived chemokine", Int lmmunol 11, 81-88 (1999).
Jacobs, J.F., et al. "Prognostic significance and mechanism of Treg infiltration in human brain tumors", J Neuroimmunol 225, 195-199 (2010).
Jansen et al., "Immunotoxins: Hybrid Molecules Combining High Specificity and Potent Cytotoxicity", Immunological Reviews 62: 185-216 (1982).
Kadin M. et al. "Systemic and Primary Cutaneous Anaplastic Large Cell Lymphomas", Seminars in Hematology, 40:244-256, (2003).
Kaplitt, M. G. et al., "Long-term gene expression and phenotypic correction using adeno-associated virus vectors in the mammalian bran", Nat. Genet. 8:148 (1994).
Killen and Lindstrom, "Specific killing of lymphocytes that cause experimental autoimmune myasthenia gravis by ricin toxin-acetylcholine receptor conjugates", Jour. Immun. 133:1335-2549 (1984).
Kim, Y.H. et al. "Long-term Outcome of 525 Patients with Mycosis Fungoides and Sezary Syndrome", Arch Dermatol, 139:857-866 (2003).
Kohler and Milstein, "Continuous cultures of fused cells secreting antibody of predefined specificity", Nature, 256:495 (1975).
Kohm, A.P., et al. "Cutting Edge: Anti-CD25 monoclonal antibody injection results in the functional inactivation, not depletion, of CD4+CD25+ T regulatory cells", J Immunol. 176, 3301-3305 (2006).
Kozbor, "A human hybrid myeloma for production of human monoclonal antibodies", J. Immunol., 133:3001 (1984).
Kozbor, et al., "The production of monoclonal antibodies from human lymphocytes", Immunol Today 4: 72 (1983).
Labrijn, AF. et al, "Species-Specific Determinants in the IgG CH3 Domain Enable Fab-Arm Exchange by Affecting the Noncovalent CH3-CH3 Interaction Strength", Journal of Immunol 187:3238-3246, (2011).

(56) References Cited

OTHER PUBLICATIONS

Lam K. "Application of combinatorial library methods in cancer research and drug discovery", Anticancer Drug Design 12: 145, (1997).
Lam K. et al. "A new type of synthetic peptide library for identifying ligand-binding activity", Nature 354: 82-84, (1991).
Le Gal La Salle et al., "An Adenovirus Vector for Gene Transfer into Neurons and Glia in the Brain", Science, 259:988 (1993).
Levings, M.K. et al "Human cd25+cd4+ T regulatory cells suppress naive and memory T cell proliferation and can be expanded in vitro without loss of function", J Exp Med 193, 1295-1302 (2001).
Lonberg et al., "Antigen-specific human antibodies from mice comprising four distinct genetic modifications", Nature 368 856-859 (1994).
Lonberg and Huszar, "Human Antibodies from Transgenic Mice", Intern. Rev. Immunol. 13 65-93 (1995).
Mahnke, K., et al. Depletion of CD4+CD25+ human regulatory T cells in vivo: kinetics of Treg depletion and alterations in immune functions in vivo and in vitro, Int J Cancer 120, 2723-2733 (2007).
Malmqvist, M. "Biospecific interaction analysis using biosensor technology", Nature 361: 186-87 (1993).
Marasco et al., "Design, intracellular expression, and activity of a human anti-human immunodeficiency virus type 1 gp120 single-chain antibody", Proc. Natl. Acad. Sci. USA, 90: 7889-7893 (1993).
Marks et al., "By-passing Immunization. Human Antibodies from V-gene Libraries Displayed on Phage", J. Mol. Biol., 222:581 (1991).
Marks et al. "By-passing Immunization: Building High Affinity Human Antibodies by Chain Shuffling", Bio/Technology 10, 779-783 (1992).
Martin et al. "Irreversible Coupling of Immunoglobulin Fragments to Preformed Vesicles", J. Biol. Chem., 257: 286-288 (1982).
Mizukami, Y. et al. "CCL17 and CCL22 chemokines within tumor microenvironment are related to accumulation of Foxp3+ regulatory T cells in gastric cancer" Int J Cancer 122, 2286-2293 (2008).
Morrison, "Success in specification", Nature 368, 812-13 (1994).
Morrison et al., "High-flow microinfusion: tissue penetration and pharmacodynamics", Am. J. Physiol. 266:292-305 (1994).
Munson and Rodbard, "Ligand: A Versatile Computerized Approach for Characterization of Ligand-Binding Systems", Anal. Biochem. 107:220 (1980).
Neuberger M. "Generating high-avidity human Mabs in mice" Nature Biotechnology 14, 826 (1996).
Niens, M., et al. "Serum chemokine levels in Hodgkin lymphoma patients: highly increased levels of CCL17 and CCL22", Br J Haematol 140, 527-536 (2008).
Querfeld C. et al. "The spectrum of cutaneous T-cell lymphomas: new insights into biology and therapy", Curr Opin Hematol, 12:273-278, (2005).
Ramakrishnan, S. et al., "Comparison of the Selective Cytotoxic Effects of Immunotoxins Containing Ricin a Chain or Pokeweed Antiviral Protein and Anti-Thy 1.1 Monoclonal Antibodies", Cancer Res. 44:201-208 (1984).
Ridgway et al., "Knobs-into-holes' engineering of antibody CH3 domains for heavy chain heterodimerization", Protein Eng 7:617-621 (1996).
Roncarolo, M. G. et al. "Regulatory T -cell immunotherapy for tolerance to self antigens and alloantigens in humans", Nat Rev Immunol 7, 585-598 (2007).
Sakaguchi, S. et al. "Regulatory T cells and immune tolerance", Cell 133, 775-787 (2008).
Scott and Smith, "Searching for Peptide Ligands with an Epitope Library", Science 249: 386-390, (1990).
Shopes, "A genetically engineered human IgG mutant with enhanced cytolytic activity", J. Immunol., 148: 2918-2922 (1992).
Stevenson et al., "A chimeric antibody with dual Fc regions (bisFabFc) prepared by manipulations at the IgG hinge", Anti-Cancer Drug Design, 3: 219-230 (1989).
Van der Neut Kolfschoten, M. et al., "Anti-Inflammatory Activity of Human IgG4 Antibodies by Dynamic Fab Arm Exchange", Science 317:1554-1557 (2007).
Vitetta et al., "Redesigning Nature's Poisons to Create Anti-Tumor Reagents", Science 238: 1098 (1987).
Wagsater, D. et al. "Quantification of the chemokines CCL17 and CCL22 in human colorectal adenocarcinomas" Molecular Medicine Reports 1, 211-217 (2008).
Wilkinson D. "Ultimate Abs", The Scientist, vol. 14, No. 8, pp. 25-28 (2000).
Willemze R. et al. "WHO-EORTC classification for cutaneous lymphomas", Blood, 105:3768-3785 (2005).
Woo, E. Y., et al. Regulatory CD4+CD25+ T cells in tumors from patients with early-stage non-small cell lung cancer and late-stage ovarian cancer. Cancer Res 61, 4766-4772 (2001).
Wood, K.J. & Sakaguchi, S. "Regulatory T cells in transplantation tolerance", Nat Rev Immunol 3, 199-210 (2003).
Yamanaka K. et al. "Decreased T-Cell Receptor Excision Circles in Cutaneous T-Cell Lymphoma", Clin Cancer Res, 11:5748-5755 (2005).
Yang, et al., "Cellular and Humoral Immune Responses to Viral Antigens Create Barriers to Lung-Directed Gene Therapy with Recombinant Adenoviruses", J. Virol. 69:2004 (1995).
Yawalkar N. et al. "Profound loss of T-cell receptor repertoire complexity in cutaneous T-cell lymphoma", Blood, 102:4059-4066 (2003).
Yu, P., et al. "Intratumor depletion of CD4+cells unmasks tumor immunogenicity leading to the rejection of late-stage tumors", J Exp Med 201, 779-791 (2005).
Zebedee et al., "Human combinatorial antibody libraries to hepatitis B surface antigen", Proc. Natl. Acad. Sci. USA 89:3175-79 (1992).
Zou, W. "Regulatory T cells, tumour immunity and immunotherapy", Nat Rev Immunol 6, 295-307 (2006).
Zuckermann, et al., "Discovery of Nanomolar Ligands for 7-Transmembrane G-Protein-Coupled Receptors from a Diverse N-(Substituted)glycine Peptoid Library", J. Med. Chem. 37: 2678 (1994).
Chang et al., "Humanization of an Anti-CCR4 Antibody that Kills Cutaneous T-Cell Lymphoma Cells and Abrogates Suppression by T-Regulatory Cells" Molecular Cancer Therapeutics, vol. 11, No. 11, (Nov. 1, 2012), pp. 2451-2461.
Salfeld "Isotype Selection in Antibody Engineering", Nature Biotechnology, vol. 25, No. 12, pp. 1369-1372, Dec. 2007.

* cited by examiner

SEQUENCE LISTING

```
<160> NUMBER OF SEQ ID NOS: 46

<210> SEQ ID NO 1
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 1
caggtgcagc tggtgcagag cggcgcggaa gtgaaaaaac cgggcgcgag cgtgaaagtg      60
agctgcaaag cgagcggcta tacctttgcg agcgcgtgga tgcattggat gcgccaggcg     120
ccgggccagg gcctggaatg gattggctgg attaacccgg gcaacgtgaa caccaaatat     180
```

```
aacgaaaaat ttaaaggccg cgcgaccctg accgtggata ccagcaccaa caccgcgtat    240
atggaactga gcagcctgcg cagcgaagat accgcggtgt attattgcgc gcgcagcacc    300
tattatcgcc cgctggatta ttggggccag ggcaccctgg tgaccgtgag cagc          354
```

<210> SEQ ID NO 2
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 2

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Ala
            20                  25                  30

Trp Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Arg Pro Leu Asp Tyr Trp Gly Gln Gly Thr
            100                 105                 110

Leu Val Thr Val Ser Ser
        115
```

<210> SEQ ID NO 3
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 3

```
gatattgtga tgacccagag cccggatagc ctggcggtga gcctgggcga acgcgcgacc     60
attaactgca aaagcagcca gagcattctg tatagcagca accagaaaaa ctatctggcg    120
tggtatcagc agaaaccggg ccagagcccg aaactgctga tttattgggc gagcacccgc    180
gaaagcggcg tgccggatcg ctttagcggc agcggcagcg gcaccgattt tacccctgacc   240 attagcagcc tgcaggcgga agatgtggcg gtgtattatt gccatcagta tatgagcagc    300
tatacctttg gccagggcac caaactggaa attaaa                              336
```

<210> SEQ ID NO 4
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 4

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30
```

```
Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys His Gln
                 85                  90                  95

Tyr Met Ser Ser Tyr Thr Phe Gly Gln Gly Thr Lys Leu Glu Ile Lys
            100                 105                 110
```

<210> SEQ ID NO 5
<211> LENGTH: 981
<212> TYPE: DNA
<213> ORGANISM: Artificial Sequence
<220> FEATURE:
<223> OTHER INFORMATION: Synthetic Polynucleotide

<400> SEQUENCE: 5

```
gcgagcacca aaggcccgag cgtgtttccg ctggcgccgt gcagccgcag caccagcgaa      60
agcaccgcgg cgctgggctg cctggtgaaa gattattttc cggaaccggt gaccgtgagc     120
tggaacagcg gcgcgctgac cagcggcgtg cataccttc cggcggtgct gcagagcagc      180
ggcctgtata gcctgagcag cgtggtgacc gtgccgagca gcagcctggg caccaaaacc     240
tatacctgca acgtggatca taaaccgagc aacaccaaag tggataaacg cgtggaaagc     300
aaatatggcc cgccgtgccc gagctgcccg gcgccggaat tctgggcgg cccgagcgtg     360
tttctgtttc cgccgaaacc gaaagatacc ctgatgatta gccgcacccc ggaagtgacc     420
tgcgtggtgg tggatgtgag ccaggaagat ccggaagtgc agtttaactg gtatgtggat     480
ggcgtggaag tgcataacgc gaaaaccaaa ccgcgcgaag aacagtttaa cagcacctat     540
cgcgtggtga gcgtgctgac cgtgctgcat caggattggc tgaacggcaa agaatataaa     600
tgcaaagtga gcaacaaagg cctgccgagc agcattgaaa aaaccattag caaagcgaaa     660
ggccagccgc gcgaaccgca ggtgtatacc ctgccgccga gcccggaaga atgaccaaa     720
aaccaggtga gcctgacctg cctggtgaaa ggcttttatc cgagcgatat tgcggtggaa     780
tgggaaagca acggccagcc ggaaaacaac tataaaacca cccgccggt gctggatagc     840
gatggcagct ttttctgta tagccgcctg accgtggata aaagccgctg caggaaggc     900
aacgtgttta gctgcagcgt gatgcatgaa gcgctgcata ccattatacc cagaaaagc     960
ctgagcctga gcctgggcaa a                                              981
```

<210> SEQ ID NO 6
<211> LENGTH: 327
<212> TYPE: PRT
<213> ORGANISM: Artificial Sequence
<220> FEATURE:
<223> OTHER INFORMATION: Synthetic Polypeptide

<400> SEQUENCE: 6

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

|  |  |  |  | 50 |  |  |  | 55 |  |  |  | 60 |  |  |
|---|---|---|---|---|---|---|---|---|---|---|---|---|---|---|
| Leu | Ser | Ser | Val | Val | Thr | Val | Pro | Ser | Ser | Leu | Gly | Thr | Lys | Thr |
| 65 |  |  |  | 70 |  |  |  | 75 |  |  |  | 80 |  |  |
| Tyr | Thr | Cys | Asn | Val | Asp | His | Lys | Pro | Ser | Asn | Thr | Lys | Val | Asp | Lys |
|  |  |  |  | 85 |  |  |  | 90 |  |  |  | 95 |  |  |
| Arg | Val | Glu | Ser | Lys | Tyr | Gly | Pro | Pro | Cys | Pro | Ser | Cys | Pro | Ala | Pro |
|  |  |  | 100 |  |  |  |  | 105 |  |  |  |  | 110 |  |  |
| Glu | Phe | Leu | Gly | Gly | Pro | Ser | Val | Phe | Leu | Phe | Pro | Pro | Lys | Pro | Lys |
|  |  | 115 |  |  |  |  | 120 |  |  |  |  | 125 |  |  |  |
| Asp | Thr | Leu | Met | Ile | Ser | Arg | Thr | Pro | Glu | Val | Thr | Cys | Val | Val | Val |
| 130 |  |  |  |  | 135 |  |  |  |  | 140 |  |  |  |  |  |
| Asp | Val | Ser | Gln | Glu | Asp | Pro | Glu | Val | Gln | Phe | Asn | Trp | Tyr | Val | Asp |
| 145 |  |  |  |  | 150 |  |  |  |  | 155 |  |  |  |  | 160 |
| Gly | Val | Glu | Val | His | Asn | Ala | Lys | Thr | Lys | Pro | Arg | Glu | Glu | Gln | Phe |
|  |  |  |  | 165 |  |  |  |  | 170 |  |  |  |  | 175 |  |
| Asn | Ser | Thr | Tyr | Arg | Val | Val | Ser | Val | Leu | Thr | Val | Leu | His | Gln | Asp |
|  |  |  | 180 |  |  |  |  | 185 |  |  |  |  | 190 |  |  |
| Trp | Leu | Asn | Gly | Lys | Glu | Tyr | Lys | Cys | Lys | Val | Ser | Asn | Lys | Gly | Leu |
|  |  | 195 |  |  |  |  | 200 |  |  |  |  | 205 |  |  |  |
| Pro | Ser | Ser | Ile | Glu | Lys | Thr | Ile | Ser | Lys | Ala | Lys | Gly | Gln | Pro | Arg |
| 210 |  |  |  |  | 215 |  |  |  |  | 220 |  |  |  |  |  |
| Glu | Pro | Gln | Val | Tyr | Thr | Leu | Pro | Pro | Ser | Pro | Glu | Glu | Met | Thr | Lys |
| 225 |  |  |  |  | 230 |  |  |  |  | 235 |  |  |  |  | 240 |
| Asn | Gln | Val | Ser | Leu | Thr | Cys | Leu | Val | Lys | Gly | Phe | Tyr | Pro | Ser | Asp |
|  |  |  |  | 245 |  |  |  |  | 250 |  |  |  |  | 255 |  |
| Ile | Ala | Val | Glu | Trp | Glu | Ser | Asn | Gly | Gln | Pro | Glu | Asn | Asn | Tyr | Lys |
|  |  |  | 260 |  |  |  |  | 265 |  |  |  |  | 270 |  |  |
| Thr | Thr | Pro | Pro | Val | Leu | Asp | Ser | Asp | Gly | Ser | Phe | Phe | Leu | Tyr | Ser |
|  |  | 275 |  |  |  |  | 280 |  |  |  |  | 285 |  |  |  |
| Arg | Leu | Thr | Val | Asp | Lys | Ser | Arg | Trp | Gln | Glu | Gly | Asn | Val | Phe | Ser |
| 290 |  |  |  |  | 295 |  |  |  |  | 300 |  |  |  |  |  |
| Cys | Ser | Val | Met | His | Glu | Ala | Leu | His | Asn | His | Tyr | Thr | Gln | Lys | Ser |
| 305 |  |  |  |  | 310 |  |  |  |  | 315 |  |  |  |  | 320 |
| Leu | Ser | Leu | Ser | Leu | Gly | Lys |  |  |  |  |  |  |  |  |  |
|  |  |  |  | 325 |  |  |  |  |  |  |  |  |  |  |  |

```
<210> SEQ ID NO 7
<211> LENGTH: 975
<212> TYPE: DNA
<213> ORGANISM: Artificial Sequence
<220> FEATURE:
<223> OTHER INFORMATION: Synthetic Polynucleotide

<400> SEQUENCE: 7
accaaaggcc cgagcgtgtt tccgctggcg ccgtgcagcc gcagcaccag cgaaagcacc      60
gcggcgctgg gctgcctggt gaaagattat tttccggaac cggtgaccgt gagctggaac     120
agcggcgcgc tgaccagcgg cgtgcatacc tttccggcgg tgctgcagag cagcggcctg     180
tatagcctga gcagcgtggt gaccgtgccg agcagcagcc tgggcaccaa aacctatacc     240
tgcaacgtgg atcataaacc gagcaacacc aaagtggata aacgcgtgga aagcaaatat     300
ggcccgccgt gcccgccgtg cccggcgccg gaatttctgg gcggcccgag cgtgtttctg     360
tttccgccga aaccgaaaga taccctgatg attagccgca ccccggaagt gacctgcgtg     420
gtggtggatg tgagccagga agatccggaa gtgcagttta ctggtatgt ggatggcgtg     480
```

```
gaagtgcata acgcgaaaac caaaccgcgc gaagaacagt ttaacagcac ctatcgcgtg    540
gtgagcgtgc tgaccgtgct gcatcaggat tggctgaacg gcaaagaata taaatgcaaa    600
gtgagcaaca aaggcctgcc gagcagcatt gaaaaaacca ttagcaaagc gaaaggccag    660
ccgcgcgaac cgcaggtgta taccctgccg ccgagcccgg aagaaatgac caaaaaccag    720
gtgagcctga cctgcctggt gaaaggcttt tatccgagcg atattgcggt ggaatgggaa    780
agcaacggcc agccggaaaa caactataaa accaccccgc cggtgctgga tagcgatggc    840
agcttttttc tgtatagcaa actgaccgtg gataaaagcc gctggcagga aggcaacgtg    900
tttagctgca gcgtgatgca tgaagcgctg cataaccatt atacccagaa aagcctgagc    960
ctgagcctgg gcaaa    975
```

<210> SEQ ID NO 8
<211> LENGTH: 325
<212> TYPE: PRT
<213> ORGANISM: Artificial Sequence
<220> FEATURE:
<223> OTHER INFORMATION: Synthetic Polypeptide

<400> SEQUENCE: 8

```
Thr Lys Gly Pro Ser Val Phe Pro Leu Ala Pro Cys Ser Arg Ser Thr
1               5                   10                  15

Ser Glu Ser Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Ser
    50                  55                  60

Ser Val Val Thr Val Pro Ser Ser Ser Leu Gly Thr Lys Thr Tyr Thr
65                  70                  75                  80

Cys Asn Val Asp His Lys Pro Ser Asn Thr Lys Val Asp Lys Arg Val
                85                  90                  95

Glu Ser Lys Tyr Gly Pro Pro Cys Pro Pro Cys Pro Ala Pro Glu Phe
            100                 105                 110

Leu Gly Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser Gln Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Tyr Arg Val Val Ser Val Leu Thr Val Leu His Gln Asp Trp Leu
            180                 185                 190

Asn Gly Lys Glu Tyr Lys Cys Lys Val Ser Asn Lys Gly Leu Pro Ser
        195                 200                 205

Ser Ile Glu Lys Thr Ile Ser Lys Ala Lys Gly Gln Pro Arg Glu Pro
    210                 215                 220

Gln Val Tyr Thr Leu Pro Pro Ser Pro Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270
```

Pro Pro Val Leu Asp Ser Asp Gly Ser Phe Phe Leu Tyr Ser Lys Leu
            275                 280                 285

Thr Val Asp Lys Ser Arg Trp Gln Glu Gly Asn Val Phe Ser Cys Ser
        290                 295                 300

Val Met His Glu Ala Leu His Asn His Tyr Thr Gln Lys Ser Leu Ser
305                 310                 315                 320

Leu Ser Leu Gly Lys
            325

<210> SEQ ID NO 9
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 9

Gly Tyr Thr Phe Ala Ser Ala Trp
1               5

<210> SEQ ID NO 10
<211> LENGTH: 12
<212> TYPE: PRT
<213> ORGANISM: Artificial Sequence
<220> FEATURE:
<223> OTHER INFORMATION: Synthetic Oligopeptide

<400> SEQUENCE: 10

Gln Ser Ile Leu Tyr Ser Ser Asn Gln Lys Asn Tyr
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 11

Ile Asn Pro Gly Asn Val Asn Thr
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 12

Trp Ala Ser Thr Arg Glu
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 13

Ser Thr Tyr Tyr Arg Pro Leu Asp Tyr
1               5

<210> SEQ ID NO 14

<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 14

His Gln Tyr Met Ser Ser Tyr Thr
1               5

<210> SEQ ID NO 15
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 15
caggtgcagc tggtgcagag cggagccgag gtgaagaagc tggagcttc cgtcaaggtg      60 tcctgcaagg ccagcggcta caccttcgcc agccaatgga tgcactggat gcggcaggca    120
cctggacagg gcctcgaatg gatcggctgg atcaaccccg gcaacgtgaa caccaagtac    180
aacgagaagt tcaagggcag ggccaccctg accgtggaca ccagcaccaa caccgcctac    240
atggaactga gcagcctgcg gagcgaggac accgccgtgt actactgcgc cagaagcacc    300
tggtaccggc cgctggacta ctggggccag ggcacccctgg tgaccgtgag cagc          354

<210> SEQ ID NO 16
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Gln
            20                  25                  30

Trp Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Trp Tyr Arg Pro Leu Asp Tyr Trp Gly Gln Gly Thr
            100                 105                 110

Leu Val Thr Val Ser Ser
        115

<210> SEQ ID NO 17
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 17
gacatcgtga tgacccagag ccccgacagc ctggccgtga gcctgggcga gcgggccacc      60

```
atcaactgca agagcagcca gagcatcctg tacagcagca accagaagaa ctacctggcc    120
tggtatcagc agaagcccgg ccagagcccc aagctgctga tctactgggc cagcacccgg    180
gagagcggcg tgcccgaccg gtttagcggc agcggctccg gcaccgactt caccctgacc    240
atcagcagcc tgcaggccga ggacgtggcc gtgtactact gccaccagta catcagcagc    300
tacaccttcg gccagggcac aaagctggaa atcaag                              336
```

<210> SEQ ID NO 18
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 18

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Ile Ser Ser Tyr Thr Phe Gly Gln Gly Thr Lys Leu Glu Ile Lys
            100                 105                 110
```

<210> SEQ ID NO 19
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 19

```
caggtgcagc tggtgcagag cggagccgag gtgaagaagc ctggagcttc cgtcaaggtg    60
tcctgcaagg ccagcggcta caccttcgcc agcagctgga tgcactggat gcggcaggca    120
cctggacagg gcctcgaatg gatcggctgg atcaaccccg caacgtgaa caccaagtac    180 aacgagaagt tcaagggcag ggccaccctg accgtggaca ccagcaccaa caccgcctac    240
atggaactga gcagcctgcg gagcgaggac accgccgtgt actactgcgc cagaagcacg    300
tggtatcggc cgaatgacta ctggggccag ggcaccctgg tgaccgtgag cagc          354
```

<210> SEQ ID NO 20
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Ser
            20                  25                  30
```

Trp Met His Trp Met Arg Gln Ala Pro Gly Gln Gly Leu Glu Trp Ile
         35                  40                  45

Gly Trp Ile Asn Pro Gly Asn Val Asn Thr Lys Tyr Asn Glu Lys Phe
 50                  55                  60

Lys Gly Arg Ala Thr Leu Thr Val Asp Thr Ser Thr Asn Thr Ala Tyr
65                   70                  75                  80

Met Glu Leu Ser Ser Leu Arg Ser Glu Asp Thr Ala Val Tyr Tyr Cys
                 85                  90                  95

Ala Arg Ser Thr Trp Tyr Arg Pro Asn Asp Tyr Trp Gly Gln Gly Thr
            100                 105                 110

Leu Val Thr Val Ser Ser
        115

<210> SEQ ID NO 21
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 21
gacatcgtga tgacccagag ccccgacagc ctggccgtga gcctgggcga gcgggccacc      60
atcaactgca agagcagcca gagcatcctg tacagcagca accagaagaa ctacctggcc     120
tggtatcagc agaagcccgg ccagagcccc aagctgctga tctactgggc cagcacccgg     180
gagagcggcg tgcccgaccg gtttagcggc agcggctccg gcaccgactt caccctgacc     240
atcagcagcc tgcaggccga ggacgtggcc gtgtactact gccaccagta caaaagcagc     300
tacaccttcg gccagggcac aaagctggaa atcaag                              336

<210> SEQ ID NO 22
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 22

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
 50                 55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Lys Ser Ser Tyr Thr Phe Gly Gln Gly Thr Lys Leu Glu Ile Lys
            100                 105                 110

<210> SEQ ID NO 23
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 23

```
caggtgcagc tggtgcagag cggagccgag gtgaagaagc ctggagcttc cgtcaaggtg      60
tcctgcaagg ccagcggcta caccttcgcc agcagctgga tgcactggat gcggcaggca     120
cctggacagg gcctcgaatg gatcggctgg atcaacccccg gcaacgtgaa caccaagtac    180
aacgagaagt tcaagggcag ggccaccctg accgtggaca ccagcaccaa caccgcctac    240
atggaactga gcagcctgcg gagcgaggac accgccgtgt actactgcgc cagaaccacc    300
cgttatcggc ccctggacta ctggggccag ggcaccctgg tgaccgtgag cagc          354
```

<210> SEQ ID NO 24
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Ser
            20                  25                  30

Trp Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Thr Arg Tyr Arg Pro Leu Asp Tyr Trp Gly Gln Gly Thr
            100                 105                 110

Leu Val Thr Val Ser Ser
        115
```

<210> SEQ ID NO 25
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 25

```
gacatcgtga tgacccagag cccccgacagc ctggccgtga gcctgggcga gcgggccacc    60
atcaactgca gagcagcca gagcatcctg tacagcagca accagaagaa ctacctggcc    120
tggtatcagc agaagcccgg ccagagcccc aagctgctga tctactgggc cagcacccgg   180
gagagcggcg tgcccgaccg gtttagcggc agcggctccg gcaccgactt cacccctgacc   240
atcagcagcc tgcaggccga ggacgtggcc gtgtactact gccaccagta ccgtagcagc    300
tacaccttcg gccagggcac aaagctggaa atcaag                             336
```

<210> SEQ ID NO 26
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 26

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
50                      55                  60

Pro Asp Arg Phe Ser Gly Ser Gly Ser Gly Thr Asp Phe Thr Leu Thr
65                      70                  75                  80

Ile Ser Ser Leu Gln Ala Glu Asp Val Ala Val Tyr Tyr Cys His Gln
                85                  90                  95

Tyr Arg Ser Ser Tyr Thr Phe Gly Gln Gly Thr Lys Leu Glu Ile Lys
            100                 105                 110
```

<210> SEQ ID NO 27
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 27

```
caggtgcagc tggtgcagag cggagccgag gtgaagaagc ctggagcttc cgtcaaggtg      60
tcctgcaagg ccagcggcta caccttcgcc agcaatata tgcactggat gcggcaggca     120
cctggacagg gcctcgaatg gatcggctgg atcaacccg caacgtgaa caccaagtac     180
aacgagaagt tcaagggcag ggccaccctg accgtggaca ccagcaccaa caccgcctac     240
atggaactga gcagcctgcg gagcgaggac accgccgtgt actactgcgc cagactgacc     300
tattatcggc cgccggacta ctggggccag ggcaccctgg tgaccgtgag cagc            354
```

<210> SEQ ID NO 28
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 28

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Gln
            20                  25                  30

Tyr Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
50                      55                  60

Lys Gly Arg Ala Thr Leu Thr Val Asp Thr Ser Thr Asn Thr Ala Tyr
65                      70                  75                  80

Met Glu Leu Ser Ser Leu Arg Ser Glu Asp Thr Ala Val Tyr Tyr Cys
                85                  90                  95

Ala Arg Leu Thr Tyr Tyr Arg Pro Pro Asp Tyr Trp Gly Gln Gly Thr
            100                 105                 110

Leu Val Thr Val Ser Ser
        115
```

<210> SEQ ID NO 29
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 29

```
gacatcgtga tgacccagag ccccgacagc ctggccgtga gcctgggcga gcgggccacc      60
atcaactgca agagcagcca gagcatcctg tacagcagca accagaagaa ctacctggcc     120
tggtatcagc agaagcccgg ccagagcccc aagctgctga tctactgggc cagcacccgg     180
gagagcggcg tgcccgaccg gtttagcggc agcggctccg gcaccgactt caccctgacc     240
atcagcagcc tgcaggccga ggacgtggcc gtgtactact gccaccagta ctatagcagc     300
tacaccttcg gccagggcac aaagctggaa atcaag                               336
```

<210> SEQ ID NO 30
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Ser Tyr Thr Phe Gly Gln Gly Thr Lys Leu Glu Ile Lys
            100                 105                 110

<210> SEQ ID NO 31
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 31

Gly Tyr Thr Phe Ala Ser Tyr Tyr
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 32

Gly Tyr Thr Phe Ala Ser Tyr Tyr
1               5

```
<210> SEQ ID NO 33
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 33

Gly Tyr Thr Phe Ala Ser Ser Trp
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 34

Ser Thr Trp Tyr Arg Pro Leu Asp Tyr
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 35

Ser Thr Trp Tyr Arg Pro Asn Asp Tyr
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 36

Thr Thr Arg Tyr Arg Pro Leu Asp Tyr
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 37

Leu Thr Tyr Tyr Arg Pro Pro Asp Tyr
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 38

His Gln Tyr Leu Ser Ser Tyr Thr
1               5

<210> SEQ ID NO 39
```

```
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 39

His Gln Tyr Ile Ser Ser Tyr Thr
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 40

His Gln Tyr Lys Ser Ser Tyr Thr
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 41

His Gln Tyr Arg Ser Ser Tyr Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 42

His Gln Tyr Tyr Ser Ser Tyr Thr
1               5

<210> SEQ ID NO 43
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 43
caggtgcagc tggtgcagag cggagccgag gtgaagaagc tggagcttc  cgtcaaggtg      60 tcctgcaagg ccagcggcta caccttcgcc agctactaca tgcactggat gcggcaggca     120
cctggacagg gcctcgaatg gatcggctgg atcaacccg  gcaacgtgaa caccaagtac     180
aacgagaagt tcaagggcag ggccaccctg accgtgaca  ccagcaccaa caccgcctac     240
atggaactga gcagcctgcg gagcgaggac accgccgtgt actactgcgc cagaagcacc     300
tactaccggc ccctggacta ctggggccag ggcaccctgg tgaccgtgag cagc           354

<210> SEQ ID NO 44
<211> LENGTH: 118
<212> TYPE: PRT
<213> ORGANISM: Artificial Sequence
<220> FEATURE:
<223> OTHER INFORMATION: Synthetic Polypeptide
```

<400> SEQUENCE: 44

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Ala Ser Tyr
            20                  25                  30
Tyr Met His Trp Met Arg Gln Ala Pro Gly Gln Gly Leu Glu Trp Ile
        35                  40                  45
Gly Trp Ile Asn Pro Gly Asn Val Asn Thr Lys Tyr Asn Glu Lys Phe
    50                  55                  60
Lys Gly Arg Ala Thr Leu Thr Val Asp Thr Ser Thr Asn Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Thr Tyr Tyr Arg Pro Leu Asp Tyr Trp Gly Gln Gly Thr
            100                 105                 110
Leu Val Thr Val Ser Ser
        115
```

<210> SEQ ID NO 45
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 45

```
gacatcgtga tgacccagag ccccgacagc ctggccgtga gcctgggcga gcgggccacc      60
atcaactgca agagcagcca gagcatcctg tacagcagca accagaagaa ctacctggcc     120
tggtatcagc agaagcccgg ccagagcccc aagctgctga tctactgggc cagcacccgg     180
gagagcggcg tgcccgaccg gtttagcggc agcggctccg gcaccgactt caccctgacc     240
atcagcagcc tgcaggccga ggacgtggcc gtgtactact gccaccagta cctgagcagc     300
tacaccttcg gccagggcac aaagctggaa atcaag                               336
```

<210> SEQ ID NO 46
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 46

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Ile Leu Tyr Ser
            20                  25                  30
Ser Asn Gln Lys Asn Tyr Leu Ala Trp Tyr Gln Gln Lys Pro Gly Gln
        35                  40                  45
Ser Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys His Gln
                85                  90                  95

Tyr Leu Ser Ser Tyr Thr Phe Gly Gln Gly Thr Lys Leu Glu Ile Lys
                100                 105                 110
```

HUMANIZED CC CHEMOKINE RECEPTOR 4 (CCR4) ANTIBODIES AND METHODS OF USE THEREOF

RELATED APPLICATIONS

This application is a national stage entry of PCT Application No. PCT/US2015/054202, filed on Oct. 6, 2015, which claims priority to and the benefit of U.S. Provisional Application No. 62/060,381, filed on Oct. 6, 2014, the contents of which are incorporated by reference in its entirety.

GOVERNMENT INTEREST

This invention was made with government support under grant number CA093683 awarded by The National Institutes of Health. The government has certain rights in the invention.

FIELD OF THE INVENTION

This invention relates generally to the anti-CCR4 monoclonal antibodies having an IgG4 Fc domain, as well as to methods for use thereof.

INCORPORATION-BY-REFERENCE OF SEQUENCE LISTING

The contents of the text file named "DFCI-094_001WO_ST25.txt", which was created on Oct. 5, 2015 and is 32 kilobytes in size, are hereby incorporated by reference in their entirety.

BACKGROUND OF THE INVENTION

Cutaneous T cell lymphoma (CTCLs) is the second most common extranodal non-Hodgkin's T cell lymphomas in adults. A recent WHO-EORTC consensus classification (Willemze R. et al. Blood 2005, 105:3768-3785) indicates that there are thirteen clinically and histologically distinct types of CTCL; however, 90% of CTCLs fall into three classes; mycosis fungoides (MF), primary cutaneous anaplastic large cell lymphoma (ALCL), and Sezary syndrome. The most common type of CTCL, mycosis fungoides, is characterized by erythematous patches and plaques that most commonly contain CD4$^+$ T cells that show an affinity for the epidermis, or epidermotropism (Willemze R. et al. Blood 2005, 105:3768-3785). Staging is based upon a TNM classification; patients with Stage 1A disease have normal life expectancies, while patients with Stage 1B or greater have a diminished life expectancy (Kim, Y. H. et al. Arch Dermatol 2003, 139:857-866). Patients with Stage II-IV disease have a median survival of less than five years, with large cell transformation often leading to accelerated deterioration (Kim, Y. H. et al. Arch Dermatol 2003, 139:857-866). Sezary syndrome is a leukemic variant of CTCL wherein clonal CD4$^+$ T cells accumulate in blood and lymph nodes as well as skin; five year survival is less than 25%. Primary cutaneous ALCL has a much less aggressive course, with a five year survival of 95%; however, cutaneous ALCL with concurrent nodal involvement is more aggressive (Willemze R. et al. Blood 2005, 105:3768-3785; Kadin M E, Carpenter C. Semin Hematol 2003, 40:244-256).

There is significant immune dysfunction in CTCL patients, with global dysregulation of the T cell repertoire of unknown etiology (Yamanaka K. et al. Clin Cancer Res 2005, 11:5748-5755; Yawalkar N. et al. Blood 2003, 102: 4059-4066). The terminal event in most patients is bacterial sepsis. Current therapies for advanced MF and Sezary syndrome are palliative and durable long-term remissions are rare (Querfeld C. et al. Curr Opin Hematol 2005, 12:273-278). Thus, there is an urgent need for more effective therapies.

Current hypotheses indicate that aberrant T-cell activity is a likely driver in the pathophysiology of CTCL. Of particular importance is the observation that malignant T-cells may play a role akin to regulatory T cells and as such supress antitumor activity in CTCL. The CC chemokine receptor 4 (CCR4) is expressed at high levels on malignant, skin homing T-cells that are present in CTCL, as well as on regulatory T-cells (Tregs). Tumor cells secrete the chemokines CCL17 and CCL22 which are ligands for CCR4. In turn, secretion of these ligands attracts regulatory T-cells and malignant T-cells to the sites of the tumor, which results in a suppression of effector T-cells in the cancer cell environment. This suppression of the effector T-cells results in a favourable environment for continued cancer cell growth.

Previous work indicated that the use of a humanized anti-CCR4 monoclonal antibody, mAb2-3 IgG1, reduced the migration of regulatory T cells toward the CCR4 ligands, and ultimately resulted in a decrease of tumor size in in vivo tumor models. Regulation of both the migratory ability of regulatory and malignant T-cells toward the tumor cells, as well as direct cellular toxicity of the malignant cells, plays a key role in the progression of the cancer.

SUMMARY OF THE INVENTION

The invention provides an isolated humanized monoclonal antibody that binds to the human CC chemokine receptor 4 (CCR4) and has an IgG4 heavy chain constant region The invention further provides an antibody containing a $V_H$ amino acid sequence having SEQ ID NO: 2 and a $V_L$ amino acid sequence having SEQ ID NO: 4; a $V_H$ amino acid sequence having SEQ ID NO: 16 and a $V_L$ amino acid sequence having SEQ ID NO: 18; a $V_H$ amino acid sequence having SEQ ID NO: 20 and a $V_L$ amino acid sequence having SEQ ID NO: 22; a $V_H$ amino acid sequence having SEQ ID NO: 24 and a $V_L$ amino acid sequence having SEQ ID NO: 26; a $V_H$ amino acid sequence having SEQ ID NO: 28 and a $V_L$ amino acid sequence having SEQ ID NO: 30; or a $V_H$ amino acid sequence having SEQ ID NO: 44 and a $V_L$ amino acid sequence having SEQ ID NO: 46 and a heavy chain constant region having SEQ ID NO: 6 or SEQ ID: 8.

The antibodies according to the invention have a binding affinity of about 1.5 nM$^{-1}$ or less.

The invention also provides a antibody that is a bi-specific antibody containing the antibody according to the invention and the heavy-light chain of an antibody that recognizes a second antigen. For example, the second antigen is a tumor associated antigen or a T-cell function modulating molecule. The tumor associated antigen is for example CA-IX, ErbB2 or HVEM. The T-cell function modulating molecule is PD-L1, GITR, IL21, IL21R, CD160, TIM3, LAG3 or GAL9

In another aspect, the invention provides a cell producing the antibodies of the invention.

In a further aspect, the antibody is linked to a therapeutic agent. The therapeutic agent is, for example a toxin, a radiolabel, a siRNA, a small molecule, or a cytokine. The cytokine is, for example, IL-2 or TGF-beta.

The invention further provides fusion proteins containing the antibodies of the invention. A fusion protein is, for example, an anti-CCR4 antibody or a functional fragment thereof, operably linked to a cytokine or growth factor, such as an IL-2 or TGF-beta polypeptide.

The invention further provides methods for increasing T cell proliferation by contacting a T cell with a fusion protein containing an anti-CCR4 antibody operably linked to a cytokine.

In some aspects the invention provides a method of inhibiting the migration of regulatory T-cells (Tregs) in a subject by administering to the subject an antibody according to the invention. The lymphocytes, effector T-cells or Tregs are not depleted.

Also included in the invention is a method for augmenting an immune response to an antigen by contacting the antigen an antibody according to the invention. In a further aspect, the antibody is administered prior to or after exposure to the antigen. The administration of the antibody of the present invention causes an increase in antigen-specific T-cell activity. In another aspect, the administration of the antibody of the present invention causes an increase in T-cell proliferation. For example, the T cell is an effector T-cell. For example, the antigen is a viral antigen, a bacterial antigen, or a tumor associated antigen. In one aspect, the viral antigen is, for example, HIV.

The invention also provides a method for reversing regulatory T cell-mediated suppression of effector T cell proliferation comprising contacting a T cell with an antibody according to the invention.

In another aspect, the invention provides a method for treating or alleviating a symptom of cancer by administering to a subject in need thereof a composition including an antibody according to the invention. The cancer is, for example, a solid cancer or a hematologic cancer. Exemplary hematologic cancers include, but are not limited to: cutaneous T-cell lymphoma (CTCL), mycosis fungoides (MF), primary cutaneous anaplastic large cell lymphoma (cutaneous ALCL), Sezary syndrome, or adult T cell Leukemia/Lymphoma (ATLL). Exemplary solid cancers include, but are not limited to: renal cell carcinoma, breast cancer, lung cancer, ovarian cancer, prostate cancer, colon cancer, cervical cancer, brain cancer, liver cancer, pancreatic cancer, kidney or stomach cancer. The cancer is a solid cancer or a cancer that overexpresses CA IX, PD-L1, or HVEM.

The administration routes, in any methods of this disclosure, include, but are not limited to parenteral, (e.g., intravenous), intradermal, subcutaneous, oral (e.g., inhalation), transdermal (i.e., topical), transmucosal, and rectal administration.

The subject in any methods of this disclosure is, for example, a mammal. The mammal is, for example, a human.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims

DETAILED DESCRIPTION

Figure 1:
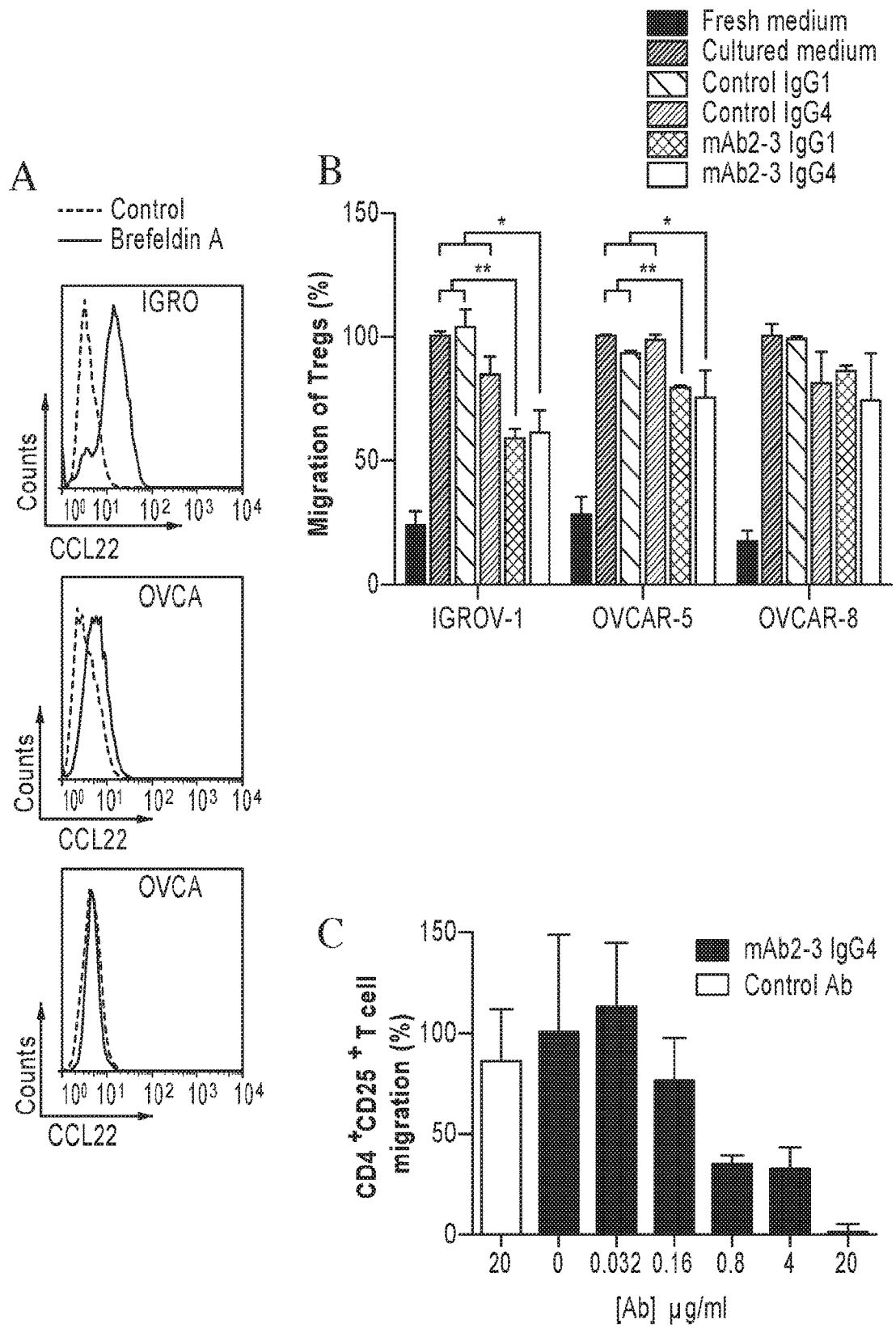
FIG. 1. mAb2-3 mediates inhibition of Treg migration. (A) The CCL22 expression on ovarian cancer cell lines is shown. Cancer cells were treated with or without brefeldin-A. After a 4-hour treatment, cells were harvested, stained with anti-CCR4 antibody, and then analyzed by flow cytometry. (B) In vitro chemotaxis of CD4+CD25+ T cells induced by CCL22-expressing ovarian cancer cell supernatant was inhibited by mAb2-3, but not by the control antibody. (C) Chemoattraction of human lymphocytes by 100 nM CCL22 is inhibited by mAb2-3 in a dose dependent manner. Results were expressed as means±SD and Student's t-test. These data indicate that ovarian cancer cell lines, IGROV-1 and OVCAR-5, are capable of CCL22 secretion and may significantly contribute to the increased CCL22 chemoattraction on Tregs. In addition, both mAb2-3 IgG1 and IgG4 are able to inhibit the CCL22 chemoattraction on Tregs.

Chemokines are a family of secreted proteins known primarily for their roles in leukocyte activation and chemotaxis. Their specific interaction with chemokine receptors on target cells trigger signaling cascades that result in inflammatory mediator release, changes in cell shape, and cellular migration. The CC chemokine receptor 4 (CCR4) is the cognate receptor for the CC chemokines CCL17 and CCL22, and is expressed on functionally distinct subsets of T cells, including T helper type 2 cells (Th2), and the majority of regulatory T cells (Tregs) (Iellem et al., 2001; and Imai et al., 1999). Growing evidence indicate that CCL17/22 secretion promotes increased numbers of tumor-infiltrating Tregs by malignant entities such as colorectal, ovarian, Hodgkin's lymphoma and glioblastoma (Curiel et al., 2004; Wagsater et al., 2008; Niens et al., 2008; Jacobs et al., 2010; Hiraoka et al., 2006). Increased levels of Treg in tumors hinder efficient antitumor immune responses (Wood et al., 2003; and Levings et al., 2001) and are often associated with poor clinical outcome and tumor progression (Hiraoka et al., 2006; and Woo et al., 2001). Accordingly, one major obstacle of successful cancer therapies might be caused by migration of Treg into tumors and their suppression of antitumor immune responses in the tumor microenvironment (Zou et al, 2006; and Yu et al, 2005). In an effort to abrogate Treg suppressive function and consequently promote antitumor immunity, monoclonal antibodies (mAbs) as immunotherapeutics against Tregs have been evaluated in preclinical and clinical studies in recent years (Mahnke et al., 2007; Roncarolo et al., 2007). However, a caveat to systemic Treg depletion with mAb immunotherapy is its highly anticipated association with autoimmunity (Sakaguchi et al., 2008; and Kohm et al., 2006). An alternative strategy to avoid Treg induced cancer immune evasion is to develop a tumor-associated Treg targeting therapy that directly hinders Treg attraction and accumulation in tumor tissue.

One potential of mAbs in cancer immunotherapy lies in their capacity to block or modulate immunological axes which promote immune evasion by tumors. The chemokine receptor CCR4 is highly expressed on the majority of FOXP3+ Tregs, immune cells which are considered the most potent inhibitors of anti-tumor immunity and the greatest barrier to successful immunotherapy (Baatar et al., 2007). Moreover, the tumor-associated chemokines of CCR4 have been detected in patients with different types of cancer (Mizukami et al., 2008; Gobert et al., 2009; and Faget et al., 2011). Thus, the targeted approach of human anti-CCR4 mAb immunotherapy described herein offers significant advantages in improving cancer immunotherapeutic efficacy while simultaneously reducing its side effects.

The present invention provides humanized IgG4 monoclonal antibodies specific against chemokine (C-C motif) receptor 4 (CCR4). The initial humanization of the anti-CCR4 antibodies is described in WO 2009/086514 the contents of which are incorporated by reference in its entirety. The description of an optimized variant of the humanized anti-CCR antibody, Ab2-3 IgG1, is described in WO 2013/166500 the contents of which are incorporated by reference in its entirety. The antibodies were produced by humanizing a mouse anti-CCR4 monoclonal antibody, mAb1567 that recognizes the N-terminal and extracellular domains of CCR4. Unlike affinity maturation of antibodies against antigens for which pure protein is readily available, affinity maturation of anti-CCR4 antibodies was particular challenging due to 7-transmembrane structure of the protein. This complex structure of CCR4 made screening and selection affinity matured antibodies less efficient and less predictable.

A humanized, IgG4 isotype monoclonal antibody against CCR is described herein and henceforth referred to as CCR4-IgG4. CCR4 IgG4 has a different Fc domain amino acid sequence in comparison to CCR4-3 IgG1. The CCR4-3 IgG4 antibodies have affinities that are at least equal to or 1-fold, 1.5-fold, 2-fold higher than the originally described CCR4-IgG1.

The CCR4-IgG4 antibodies of the invention also effectively inhibit the chemotaxis of CD4+CD25$^{high}$ Tregs. The CCR4-IgG4 antibodies of the invention also mediate the activation of tumor-primed T-cells by inhibition of the Treg recruitment from the tunmor tissue. Importantly CCR4-IgG4 antibodies are non-immunodepleting.

Accordingly, the CCR4-IgG4 antibodies are useful in treating CCR4-expressing tumors such as cutaneous T-cell lymphoma. Additionally, the affinity optimized anti-CCR4 antibodies are also useful in the treatment of other tumors by enhancing the anti-tumor immune response, by suppressing Treg trafficking.

Cutaneous T-cell lymphomas (CTCLs) are a heterogenous group of lymphoproliferative disorders causes by clonally derived skin homing T cells. CTCL cells uniformly express CCR4. Specifically, CCR4 is a prominent feature of malignant T cells in MF, cutaneous ALCL, and roughly 50% of nodal ALCL. Unlike CLA, it is reliably expressed in Sezary syndrome and during large cell transformation of MF and is also expressed by other T lymphoid malignancies that can involve skin, such as Adult T Cell Leukemia/Lymphoma (ATLL). Expression of CCR4 is limited amongst non-malignant cells and absent on neutrophils, monocytes, or B cells. Importantly, CCR4 is absent on naïve T cells, and present on fewer than half of all memory T cells. The reliable expression of CCR4 on CTCL cells, and its limited expression on other immune cells, makes targeted therapy of CCR4 an attractive goal for these malignancies.

While some progress has been made in identifying small molecule inhibitors that are relatively selective for CCR4, specific monoclonal antibodies against CCR4 are an attractive target for immunotherapy of CTCL because of their exquisite binding specificity. In addition, the in vivo effector functions that are mediated through Fc binding to Fcγ receptors can be exploited to kill tumor cells. The precise properties of Mabs that are required for optimal in vivo immunodepleting activity are not known, but antibodies can be selected to act as either as receptor agonists or antagonists, and/or to promote or inhibit receptor dimerization and/or internalization. Different immune mechanisms of antibody-mediated tumor clearance have also been identified. For example, Mab-mediated recruitment of natural killer cells to tumors can occur through the Fc-γ activation of receptors on these immune effector cells, a process known as antibody-dependent cellular cytoxicity (ADCC). Other immune mechanisms include complement dependent cytotoxicity (CDC) and antibody dependent cellular phagocytosis (ADCP). Additional mechanisms related to intrinsic Mab activities include: blockade of ligand binding or heterodimerization, inhibition of downstream signaling of Akt, and acceleration of receptor internalization. The latter mechanism is particularly effective because ligand-induced endocytosis and degradation of active receptor tyrosine kinases (RTKs) is considered a major physiological process underlying attenuation of growth-promoting signals.

Leukocyte trafficking, which is critically regulated by chemokines and their receptors, share many of the characteristics of tumor cell infiltration and metastasis. While expression of the chemokine receptor CCR4 by tumor cells is associated with skin involvement, CCR4 also has an important role in both normal and tumor immunity. In a subset of CTCL patients with HTLV-1 associated Adult T-cell leukemia/lymphoma (ATLL), the tumor cells themselves function as regulatory T (Treg) cells, contributing to tumor survival in the face of host anti-tumor immune responses. In other types of cancers, the chemokines TARC/CCL17 and MDC/CCL22, specific ligands for CCR4 that are produced by tumor cells and the tumor microenvironment, attract CCR4+ Treg cells to the tumor, where they create a favorable environment for tumor escape from host immune responses. Thus, a therapeutic anti-CCR4 Mab is the ideal treatment modality for many different cancers, not only to directly kill the CCR4+ tumor cells, but also to overcome the suppressive effect of CCR4 Treg cells on the host immune response to tumor cells.

In one aspect the present invention provides a high affinity humanized monoclonal antibody that specifically binds CCR4 proteins that modulates T-cell recruitment without inducing lymphocyte depletion. Binding of this antibody to the CCR4 receptor, interrupts ligand or agonist binding of CCR4. Exemplary ligands or agonists that compete for binding to the CCR4, and which are blocked in the presence of the invented antibody, include, but are not limited to, CCL17, CCL22, and vMIP-III. By a variety of mechanisms, the antibody may decrease ligand-induced chemotaxis of CCR4-expressing cells, such as cutaneous T cell lymphoma cells (CTCL cells) or ovarian cancer cells. The CCR4-IgG4 antibody is monovalent or bivalent and comprises a single or double chain. The CCR4-IgG4 antibody may also be a bi-specific antibody, wherein at least one of the heavy-light chain heterodimers recognizes CCR4. Functionally, the binding affinity of the CCR4-IgG4 antibody is about 1.5 $nM^{-1}$ or less. The glycosylation of the Fc region of the antibody is modified to alter CCR4 binding or CCR4 ligand-blocking characteristics. For instance, the fucose content of the Fc region is decreased compared to wild type. Furthermore, the antibody comprises a therapeutic agent including, but not limited to, a toxin, a radiolabel, a siRNA, or a cytokine.

The CCR4-IgG4 modulates T cell migration and activity. Specifically, the CCR4-IgG4 can block, inhibit or decrease the migration of Tregs toward CCL ligands and as a result reduce the suppressor activity of Tregs, for example, regulatory T cell-mediated suppression of T cell activity. In another aspect, the CCR4-IgG4 can augment an immune response to an antigen. For example, the CCR4-IgG4 increases antigen-specific T cell activity. In other aspects, the CCR4-IgG4 restores or increases T cell proliferation, for example, effector T cell proliferation. In a further aspect, the CCR4-IgG4 activates T cells to secrete cytokines, such as IFN-γ. The CCR4-IgG4 also has a potent immunomodulation effect on regulatory T cells and effector T cells, resulting in inhibition of Treg recruitment to the tumor tissue and consequent activation of effector T cells against the tumor cells.

Unlike the previously described CCR4-IgG1, CCR4-IgG4 described herein does not induce cell death by complement-dependent cytotoxicity (CDC), antibody-dependent cellular toxicity (ADCC), antibody dependent cellular phagocytosis (ADPC), or any other known mechanism.

The nucleic acid and amino acid sequence of the engineered CCR4-IgG4 antibody is provided below in Tables 1A-2B.

Another aspect of the current invention, includes a stabilized version of the CCR4-IgG4 monoclonal antibody, wherein amino acid substitutions in the hinge region allows for antibodies that do not undergo in vivo Fab arm exchange, resulting in more efficient antibody binding.

TABLE 1A mAb2-3 IgG4 Variable Region nucleic acid sequences $V_H$ chain of mAb2-3 IgG4 (SEQ ID NO: 1)

CAGGTGCAGCTGGTGCAGAGCGGCGCGGAAGTGAAAAAACCGGGCGCGAG
CGTGAAAGTGAGCTGCAAAGCGAGCGGCTATACCTTTGCGAGCGCGTGGA
TGCATTGGATGCGCCAGGCGCCGGGCCAGGGCCTGGAATGGATTGGCTGG
ATTAACCCGGGCAACGTGAACACCAAATATAACGAAAAATTTAAAGGCCG
CGCGACCCTGACCGTGGATACCAGCACCAACACCGCGTATATGGAACTGA
GCAGCCTGCGCAGCGAAGATACCGCGGTGTATTATTGCGCGCGCAGCACC
TATTATCGCCCGCTGGATTATTGGGGCCAGGGCACCCTGGTGACCGTGAG
CAGC $V_L$ chain of mAb2-3 IgG4 (SEQ ID NO: 3)

GATATTGTGATGACCCAGAGCCCGGATAGCCTGGCGGTGAGCCTGGGCGA
ACGCGCGACCATTAACTGCAAAAGCAGCCAGAGCATTCTGTATAGCAGCA
ACCAGAAAAACTATCTGGCGTGGTATCAGCAGAAACCGGGCCAGAGCCCG
AAACTGCTGATTTATTGGGCGAGCACCCGCGAAAGCGGCGTGCCGGATCG
CTTTAGCGGCAGCGGCAGCGGCACCGATTTTACCCTGACCATTAGCAGCC
TGCAGGCGGAAGATGTGGCGGTGTATTATTGCCATCAGTATATGAGCAGC
TATACCTTTGGCCAGGGCACCAAACTGGAAATTAAA

TABLE 1B mAb2-3 IgG4 Variable Region amino acid sequences

$V_H$ chain of mAb2-3 IgG4 (SEQ ID NO: 2)

QVQLVQSGAEVKKPGASVKVSCKASGYTFASAWMHWMRQAPGQGLEWI
GWINPGNVNTKYNEKFKGRATLTVDTSTNTAYMELSSLRSEDTAVYYC
ARSTYYRPLDYWGQGTLVTVSS $V_L$ chain of mAb2-3 IgG4 (SEQ ID NO: 4)

DIVMTQSPDSLAVSLGERATINCKSSQSILYSSNQKNYLAWYQQKPGQ
SPKLLIYWASTRESGVPDRFSGSGSGTDFTLTISSLQAEDVAVYYCHQ
YMSSYTFGQGTKLEIK

TABLE 2A

Antibody 1-44 Variable Region nucleic acid sequences

$V_H$ chain of 1-44 (SEQ ID NO: 15)

CAGGTGCAGCTGGTGCAGAGCGGAGCCGAGGTGAAGAAGCCTGGAGCTTC
CGTCAAGGTGTCCTGCAAGGCCAGCGGCTACACCTTCGCCAGCCAATGGA
TGCACTGGATGCGGCAGGCACCTGGACAGGGCCTCGAATGGATCGGCTGG
ATCAACCCCGGCAACGTGAACACCAAGTACAACGAGAAGTTCAAGGGCAG
GGCCACCCTGACCGTGGACACCAGCACCAACACCGCCTACATGGAACTGA
GCAGCCTGCGGAGCGAGGACACCGCCGTGTACTACTGCGCCAGAAGCACC
TGGTACCGGCCGCTGGACTACTGGGGCCAGGGCACCCTGGTGACCGTGAG
CAGC $V_L$ chain of 1-44 (SEQ ID NO: 17)

GACATCGTGATGACCCAGAGCCCCGACAGCCTGGCCGTGAGCCTGGGCGA
GCGGGCCACCATCAACTGCAAGAGCAGCCAGAGCATCCTGTACAGCAGCA
ACCAGAAGAACTACCTGGCCTGGTATCAGCAGAAGCCCGGCCAGAGCCCC
AAGCTGCTGATCTACTGGGCCAGCACCCGGGAGAGCGGCGTGCCCGACCG
GTTTAGCGGCAGCGGCTCCGGCACCGACTTCACCCTGACCATCAGCAGCC
TGCAGGCCGAGGACGTGGCCGTGTACTACTGCCACCAGTACATCAGCAGC
TACACCTTCGGCCAGGGCACAAAGCTGGAAATCAAG

TABLE 2B

Antibody 1-44 Variable Region amino acid sequences

$V_H$ chain of 1-44 (SEQ ID NO: 16)

QVQLVQSGAEVKKPGASVKVSCKASGYTFASQWMHWMRQAPGQGLEWIGW
INPGNVNTKYNEKFKGRATLTVDTSTNTAYMELSSLRSEDTAVYYCARST
WYRPLDYWGQGTLVTVSS $V_L$ chain of 1-44 (SEQ ID NO: 18)

DIVMTQSPDSLAVSLGERATINCKSSQSILYSSNQKNYLAWYQQKPGQSP
KLLIYWASTRESGVPDRFSGSGSGTDFTLTISSLQAEDVAVYYCHQYISS
YTFGQGTKLEIK

TABLE 3A

Antibody 1-49 Variable Region nucleic acid sequences

$V_H$ chain of 1-49 (SEQ ID NO: 19)

CAGGTGCAGCTGGTGCAGAGCGGAGCCGAGGTGAAGAAGCCTGGAGCTTC
CGTCAAGGTGTCCTGCAAGGCCAGCGGCTACACCTTCGCCAGCAGCTGGA
TGCACTGGATGCGGCAGGCACCTGGACAGGGCCTCGAATGGATCGGCTGG
ATCAACCCCGGCAACGTGAACACCAAGTACAACGAGAAGTTCAAGGGCAG
GGCCACCCTGACCGTGGACACCAGCACCAACACCGCCTACATGGAACTGA
GCAGCCTGCGGAGCGAGGACACCGCCGTGTACTACTGCGCCAGAAGCACG
TGGTATCGGCCGAATGACTACTGGGGCCAGGGCACCCTGGTGACCGTGAG
CAGC

TABLE 3A-continued

Antibody 1-49 Variable Region nucleic acid sequences

$V_L$ chain of 1-49 (SEQ ID NO: 21)

GACATCGTGATGACCCAGAGCCCCGACAGCCTGGCCGTGAGCCTGGGCGA
GCGGGCCACCATCAACTGCAAGAGCAGCCAGAGCATCCTGTACAGCAGCA
ACCAGAAGAACTACCTGGCCTGGTATCAGCAGAAGCCCGGCCAGAGCCCC
AAGCTGCTGATCTACTGGGCCAGCACCCGGGAGAGCGGCGTGCCCGACCG
GTTTAGCGGCAGCGGCTCCGGCACCGACTTCACCCTGACCATCAGCAGCC
TGCAGGCCGAGGACGTGGCCGTGTACTACTGCCACCAGTACAAAAGCAGC
TACACCTTCGGCCAGGGCACAAAGCTGGAAATCAAG

TABLE 3B

Antibody 1-49 Variable Region amino acid sequences

$V_H$ chain of 1-49 (SEQ ID NO: 20)

QVQLVQSGAEVKKPGASVKVSCKASGYTFASSWMHWMRQAPGQGLEWIGW
INPGNVNTKYNEKFKGRATLTVDTSTNTAYMELSSLRSEDTAVYYCARST
WYRPNDYWGQGTLVTVSS $V_L$ chain of 1-49 (SEQ ID NO: 22)

DIVMTQSPDSLAVSLGERATINCKSSQSILYSSNQKNYLAWYQQKPGQSP
KLLIYWASTRESGVPDRFSGSGSGTDFTLTISSLQAEDVAVYYCHQYKSS
YTFGQGTKLEIK

TABLE 4A

Antibody 2-1 Variable Region nucleic acid sequences

$V_H$ chain of 2-1 (SEQ ID NO: 23)

CAGGTGCAGCTGGTGCAGAGCGGAGCCGAGGTGAAGAAGCCTGGAGCTTC
CGTCAAGGTGTCCTGCAAGGCCAGCGGCTACACCTTCGCCAGCAGCTGGA
TGCACTGGATGCGGCAGGCACCTGGACAGGGCCTCGAATGGATCGGCTGG
ATCAACCCCGGCAACGTGAACACCAAGTACAACGAGAAGTTCAAGGGCAG
GGCCACCCTGACCGTGGACACCAGCACCAACACCGCCTACATGGAACTGA
GCAGCCTGCGGAGCGAGGACACCGCCGTGTACTACTGCGCCAGAACCACC
CGTTATCGGCCCCTGGACTACTGGGGCCAGGGCACCCTGGTGACCGTGAG
CAGC $V_L$ chain of 2-1 (SEQ ID NO: 25)

GACATCGTGATGACCCAGAGCCCCGACAGCCTGGCCGTGAGCCTGGGCGA
GCGGGCCACCATCAACTGCAAGAGCAGCCAGAGCATCCTGTACAGCAGCA
ACCAGAAGAACTACCTGGCCTGGTATCAGCAGAAGCCCGGCCAGAGCCCC
AAGCTGCTGATCTACTGGGCCAGCACCCGGGAGAGCGGCGTGCCCGACCG
GTTTAGCGGCAGCGGCTCCGGCACCGACTTCACCCTGACCATCAGCAGCC
TGCAGGCCGAGGACGTGGCCGTGTACTACTGCCACCAGTACCGTAGCAGC
TACACCTTCGGCCAGGGCACAAAGCTGGAAATCAAG

TABLE 4B

Antibody 2-1 Variable Region amino acid sequences

$V_H$ chain of 2-1 (SEQ ID NO: 24)

QVQLVQSGAEVKKPGASVKVSCKASGYTFASSWMHWMRQAPGQGLEWIGW
INPGNVNTKYNEKFKGRATLTVDTSTNTAYMELSSLRSEDTAVYYCARTT
RYRPLDYWGQGTLVTVSS $V_L$ chain of 2-1 (SEQ ID NO: 26)

DIVMTQSPDSLAVSLGERATINCKSSQSILYSSNQKNYLAWYQQKPGQSP
KLLIYWASTRESGVPDRFSGSGSGTDFTLTISSLQAEDVAVYYCHQYRSS
YTFGQGTKLEIK

TABLE 5A

Antibody 2-2 Variable Region nucleic acid sequences

$V_H$ chain of 2-2 (SEQ ID NO: 27)

CAGGTGCAGCTGGTGCAGAGCGGAGCCGAGGTGAAGAAGCCTGGAGCTTC
CGTCAAGGTGTCCTGCAAGGCCAGCGGCTACACCTTCGCCAGCCAATATA
TGCACTGGATGCGGCAGGCACCTGGACAGGGCCTCGAATGGATCGGCTGG
ATCAACCCCGGCAACGTGAACACCAAGTACAACGAGAAGTTCAAGGGCAG
GGCCACCCTGACCGTGGACACCAGCACCAACACCGCCTACATGGAACTGA
GCAGCCTGCGGAGCGAGGACACCGCCGTGTACTACTGCGCCAGACTGACC
TATTATCGGCCGCCGGACTACTGGGGCCAGGGCACCCTGGTGACCGTGAG
CAGC $V_L$ chain of 2-2 (SEQ ID NO: 29)

GACATCGTGATGACCCAGAGCCCCGACAGCCTGGCCGTGAGCCTGGGCGA
GCGGGCCACCATCAACTGCAAGAGCAGCCAGAGCATCCTGTACAGCAGCA
ACCAGAAGAACTACCTGGCCTGGTATCAGCAGAAGCCCGGCCAGAGCCCC
AAGCTGCTGATCTACTGGGCCAGCACCCGGGAGAGCGGCGTGCCCGACCG
GTTTAGCGGCAGCGGCTCCGGCACCGACTTCACCCTGACCATCAGCAGCC
TGCAGGCCGAGGACGTGGCCGTGTACTACTGCCACCAGTACTATAGCAGC
TACACCTTCGGCCAGGGCACAAAGCTGGAAATCAAG

TABLE 5B

Antibody 2-2 Variable Region amino acid sequences

$V_H$ chain of 2-2 (SEQ ID NO: 28)

QVQLVQSGAEVKKPGASVKVSCKASGYTFASQYMHWMRQAPGQGLEWIGW
INPGNVNTKYNEKFKGRATLTVDTSTNTAYMELSSLRSEDTAVYYCARLT
YYRPPDYWGQGTLVTVSS $V_L$ chain of 2-2 (SEQ ID NO: 30)

DIVMTQSPDSLAVSLGERATINCKSSQSILYSSNQKNYLAWYQQKPGQSP
KLLIYWASTRESGVPDRFSGSGSGTDFTLTISSLQAEDVAVYYCHQYYSS
YTFGQGTKLEIK

TABLE 6A huCCR Variable Region nucleic acid sequences

$V_H$ chain of huCCR (SEQ ID NO: 43)

CAGGTGCAGCTGGTGCAGAGCGGAGCCGAGGTGAAGAAGCCTGGAGCTTC
CGTCAAGGTGTCCTGCAAGGCCAGCGGCTACACCTTCGCCAGCTACTACA
TGCACTGGATGCGGCAGGCACCTGGACAGGGCCTCGAATGGATCGGCTGG
ATCAACCCCGGCAACGTGAACACCAAGTACAACGAGAAGTTCAAGGGCAG
GGCCACCCTGACCGTGGACACCAGCACCAACACCGCCTACATGGAACTGA
GCAGCCTGCGGAGCGAGGACACCGCCGTGTACTACTGCGCCAGAAGCACC
TACTACCGGCCCCTGGACTACTGGGGCCAGGGCACCCTGGTGACCGTGAG
CAGC $V_L$ chain of huCCR (SEQ ID NO: 45)

GACATCGTGATGACCCAGAGCCCCGACAGCCTGGCCGTGAGCCTGGGCGA
GCGGGCCACCATCAACTGCAAGAGCAGCCAGAGCATCCTGTACAGCAGCA
ACCAGAAGAACTACCTGGCCTGGTATCAGCAGAAGCCCGGCCAGAGCCCC
AAGCTGCTGATCTACTGGGCCAGCACCCGGGAGAGCGGCGTGCCCGACCG
GTTTAGCGGCAGCGGCTCCGGCACCGACTTCACCCTGACCATCAGCAGCC
TGCAGGCCGAGGACGTGGCCGTGTACTACTGCCACCAGTACCTGAGCAGC
TACACCTTCGGCCAGGGCACAAAGCTGGAAATCAAG

TABLE 6B huCCR Variable Region, amino acid sequences

$V_H$ chain of huCCR (SEQ ID NO: 44)

QVQLVQSGAEVKKPGASVKVSCKASGYTFASYYMHWMRQAPGQGLEWIGW
INPGNVNTKYNEKFKGRATLTVDTSTNTAYMELSSLRSEDTAVYYCARST
YYRPLDYWGQGTLVTVSS $V_L$ chain of huCCR (SEQ ID NO: 46)

DIVMTQSPDSLAVSLGERATINCKSSQSILYSSNQKNYLAWYQQKPGQSP
KLLIYWASTRESGVPDRFSGSGSGTDFTLTISSLQAEDVAVYYCHQYLSS
YTFGQGTKLEIK

TABLE 7A

IgG4 Isotype Region nucleic acid sequences

IgG4 Isotype Region nucleic acids (SEQ ID NO: 5)

GCGAGCACCAAAGGCCCGAGCGTGTTTCCGCTGGCGCCGTGCAGCCGCAG
CACCAGCGAAAGCACCGCGGCGCTGGGCTGCCTGGTGAAAGATTATTTTC
CGGAACCGGTGACCGTGAGCTGGAACAGCGGCGCGCTGACCAGCGGCGTG
CATACCTTTCCGGCGGTGCTGCAGAGCAGCGGCCTGTATAGCCTGAGCAG
CGTGGTGACCGTGCCGAGCAGCAGCCTGGGCACCAAAACCTATACCTGCA
ACGTGGATCATAAACCGAGCAACACCAAAGTGGATAAAGCGTGGAAAGC
AAATATGGCCCGCCGTGCCCGAGCTGCCCGGCGCCGGAATTTCTGGGCGG
CCCGAGCGTGTTTCTGTTTCCGCCGAAACCGAAAGATACCCTGATGATTA
GCCGCACCCCGGAAGTGACCTGCGTGGTGGTGGATGTGAGCCAGGAAGAT
CCGGAAGTGCAGTTTAACTGGTATGTGGATGGCGTGGAAGTGCATAACGC
GAAAACCAAACCGCGCGAAGAACAGTTTAACAGCACCTATCGCGTGGTGA
GCGTGCTGACCGTGCTGCATCAGGATTGGCTGAACGGCAAAGAATATAAA
TGCAAAGTGAGCAACAAAGGCCTGCCGAGCAGCATTGAAAAAACCATTAG
CAAAGCGAAAGGCCAGCCGCGCGAACCGCAGGTGTATACCCTGCCGCCGA
GCCCGGAAGAAATGACCAAAAACCAGGTGAGCCTGACCTGCCTGGTGAAA
GGCTTTTATCCGAGCGATATTGCGGTGGAATGGGAAAGCAACGGCCAGCC
GGAAAACAACTATAAAACCACCCCGCCGGTGCTGGATAGCGATGGCAGCT
TTTTTCTGTATAGCCGCCTGACCGTGGATAAAAGCCGCTGGCAGGAAGGC
AACGTGTTTAGCTGCAGCGTGATGCATGAAGCGCTGCATAACCATTATAC
CCAGAAAAGCCTGAGCCTGAGCCTGGGCAAA

TABLE 7B

IgG4 Isotype Region amino acid sequences

IgG4 Isotype Region amino acid sequences
(SEQ ID NO: 6)

ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPSCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK

TABLE 7B-continued

IgG4 Isotype Region amino acid sequences

CKVSNKGLPSSIEKTISKAKGQPREPQVYTLPPSPEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

TABLE 8A

IgG4 with stabilized IgG4 core hinge, nucleic acid sequences

IgG4 Isotype Region nucleic acids (SEQ ID NO: 7)

ACCAAAGGCCCGAGCGTGTTTCCGCTGGCGCCGTGCAGCCGCAGCACCAG

CGAAAGCACCGCGGCGCTGGGCTGCCTGGTGAAAGATTATTTTCCGGAAC

CGGTGACCGTGAGCTGGAACAGCGGCGCGCTGACCAGCGGCGTGCATACC

TTTCCGGCGGTGCTGCAGAGCAGCGGCCTGTATAGCCTGAGCAGCGTGGT

GACCGTGCCGAGCAGCAGCCTGGGCACCAAAACCTATACCTGCAACGTGG

ATCATAAACCGAGCAACACCAAAGTGGATAAACGCGTGGAAAGCAAATAT

GGCCCGCCGTGCCCGCCGTGCCCGGCGCCGGAATTTCTGGGCGGCCCGAG

CGTGTTTCTGTTTCCGCCGAAACCGAAAGATACCCTGATGATTAGCCGCA

CCCCGGAAGTGACCTGCGTGGTGGTGGATGTGAGCCAGGAAGATCCGGAA

GTGCAGTTTAACTGGTATGTGGATGGCGTGGAAGTGCATAACGCGAAAAC

CAAACCGCGCGAAGAACAGTTTAACAGCACCTATCGCGTGGTGAGCGTGC

TGACCGTGCTGCATCAGGATTGGCTGAACGGCAAAGAATATAAATGCAAA

GTGAGCAACAAAGGCCTGCCGAGCAGCATTGAAAAAACCATTAGCAAAGC

GAAAGGCCAGCCGCGCGAACCGCAGGTGTATACCCTGCCGCCGAGCCCGG

AAGAAATGACCAAAAACCAGGTGAGCCTGACCTGCCTGGTGAAAGGCTTT

TATCCGAGCGATATTGCGGTGGAATGGGAAAGCAACGGCCAGCCGGAAAA

CAACTATAAAACCACCCCGCCGGTGCTGGATAGCGATGGCAGCTTTTTTC

TGTATAGCAAACTGACCGTGGATAAAAGCCGCTGGCAGGAAGGCAACGTG

TTTAGCTGCAGCGTGATGCATGAAGCGCTGCATAACCATTATACCCAGAA

AAGCCTGAGCCTGAGCCTGGGCAAA

TABLE 8B

IgG4 with stabilized IgG4 core hinge, amino acid sequences

IgG4 Isotype Region amino acid sequences (SEQ ID NO: 8)

TKGPSVFPLAPCSRSTSESTAALGCLVKDYFPEPVTVSWNSGALTSGVHT

FPAVLQSSGLYSLSSVVTVPSSSLGTKTYTCNVDHKPSNTKVDKRVESKY

GPPCPPCPAPEFLGGPSVFLFPPKPKDTLMISRTPEVTCVVVDVSQEDPE

VQFNWYVDGVEVHNAKTKPREEQFNSTYRVVSVLTVLHQDWLNGKEYKCK

TABLE 8B-continued

IgG4 with stabilized IgG4 core hinge, amino acid sequences

VSNKGLPSSIEKTISKAKGQPREPQVYTLPPSPEEMTKNQVSLTCLVKGF

YPSDIAVEWESNGQPENNYKTTPPVLDSDGSFFLYSKLTVDKSRWQEGNV

FSCSVMHEALHNHYTQKSLSLSLGK

The amino acid sequences of the heavy and light chain complementarity determining regions of selected antibodies are shown in Table 9 below.

TABLE 9

Amino Acid Sequences of Heavy and Light Chains.

| Antibody | Variable region | CDR1 | CDR2 | CDR3 |
|---|---|---|---|---|
| Mouse 1567 | VH | GYTFASYY (SEQ ID NO: 31) | INPGNVNT (SEQ ID NO: 11) | STYYRPLDY (SEQ ID NO: 13) |
| Humanized 1567 | VH | GYTFASYY (SEQ ID NO: 31) | INPGNVNT (SEQ ID NO: 11) | STYYRPLDY (SEQ ID NO: 13) |
| Ab1-44 | VH | GYTFASQW (SEQ ID NO: 32) | INPGNVNT (SEQ ID NO: 11) | STWYRPLDY (SEQ ID NO: 34) |
| Ab1-49 | VH | GYTFASSW (SEQ ID NO: 33) | INPGNVNT (SEQ ID NO: 11) | STWYRPNDY (SEQ ID NO: 35) |
| Ab2-1 | VH | GYTFASSW (SEQ ID NO: 33) | INPGNVNT (SEQ ID NO: 11) | TTRYRPLDY (SEQ ID NO: 36) |
| Ab2-2 | VH | GYTFASQY (SEQ ID NO: 33) | INPGNVNT (SEQ ID NO: 11) | LTYYRPPDY (SEQ ID NO: 37) |
| Ab2-3 | VH | GYTFASAW (SEQ ID NO: 9) | INPGNVNT (SEQ ID NO: 11) | STYYRPLDY (SEQ ID NO: 13) |
| Mouse 1567 | VL | QSILYSSNQKNY (SEQ ID NO: 10) | WASTRE (SEQ ID NO: 12) | HQYLSSYT (SEQ ID NO: 38) |
| Humanized 1567 | VL | QSILYSSNQKNY (SEQ ID NO: 10) | WASTRE (SEQ ID NO: 12) | HQYLSSYT (SEQ ID NO: 38) |
| Ab1-44 | VL | QSILYSSNQKNY (SEQ ID NO: 10) | WASTRE (SEQ ID NO: 12) | HQYISSYT (SEQ ID NO: 39) |
| Ab1-49 | VL | QSILYSSNQKNY (SEQ ID NO: 10) | WASTRE (SEQ ID NO: 12) | HQYKSSYT (SEQ ID NO: 40) |
| Ab2-1 | VL | QSILYSSNQKNY (SEQ ID NO: 10) | WASTRE (SEQ ID NO: 12) | HQYRSSYT (SEQ ID NO: 41) |
| Ab2-2 | VL | QSILYSSNQKNY (SEQ ID NO: 10) | WASTRE (SEQ ID NO: 12) | HQYYSSYT (SEQ ID NO: 42) |
| Ab2-3 | VL | QSILYSSNQKNY (SEQ ID NO: 10) | WASTRE (SEQ ID NO: 12) | HQYMSSYT (SEQ ID NO: 14) |

As described supra, CCR4-IgG4 of the present invention modulates T cell activity. In some aspects, administration of CCR4-IgG4 reverses regulatory T-cell-mediated suppression of effector T cell proliferation. Specifically, treatment with CCR4-IgG4 stimulates or increases proliferation of effector T cells (Teff), without stimulating the proliferation of regulatory T cells (Treg). Effector T cells consist of four distinct populations, as classified by CD45RA and CCR7 expression profiles: T-different types (Tdiff), naïve T cells (Tnaive), central memory T cells (Tcm) and effector memory T cells (Tem). The CCR4-IgG4 of the present invention can stimulate or increase the proliferation of any of the Teff populations. In some aspects, increasing proliferation of effector T cells increases antigen-specific T cell activity to augment an immune response to an antigen. In some aspects, augmenting effector T-cell-mediated immune response may contribute to inhibition of tumorigenesis or reduction in tumor size.

In other aspects, CCR4-IgG4 modulates T cell cytokine production and secretion. For example, administration of CCR4-IgG4 specifically increases IFN-gamma (IFNγ) production and release from T cells. In other aspects, administration of CCR4-IgG4 may not affect IL-10 or IL-4 release. In another aspect, administration of CCR4-IgG4 may not affect, or may slightly reduce TGF-beta release. Cytokine release profiles may indicate the specific T cell population activated by treatment with CCR4-IgG4, as IFNγ secretion is a characteristic of Th1 cells (T-helper type 1 cells), while TGF-beta and IL-10 secretion is characteristic of regulatory T cells and IL-4 is released by Th2 (T helper type 2 cells). In some aspects, CCR4-IgG4 stimulates T cell activity, wherein the T cells are Th1 cells. In some embodiments, CCR4-IgG4 stimulates secretion of IFNγ and decreases or does not change secretion of TGF-β, IL-10 or IL-4.

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, chimeric, dAb (domain antibody), single chain, $F_{ab}$, $F_{ab'}$ and $F_{(ab')2}$ fragments, scFvs, and $F_{ab}$ expression libraries.

A single chain Fv ("scFv") polypeptide molecule is a covalently linked $V_H::V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the term "epitope" includes any protein determinant capable of specific binding to an immunoglobulin, a scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a CCR4 epitope when the equilibrium binding constant ($K_d$) is ≤1 µM, preferably ≤100 nM, more preferably ≤10 nM, and most preferably ≤100 pM to about 1 pM, as measured by assays such as radioligand binding assays or similar assays known to those skilled in the art.

A CCR4 protein of the invention, or a derivative, fragment, analog, homolog or ortholog thereof, may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to CCR4. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the CCR4 protein, with which it is normally reactive, and then add the human monoclonal antibody being tested to determine if the human monoclonal antibody being tested is inhibited in its ability to bind CCR4. If the human monoclonal antibody being tested is inhibited then, in all likelihood, it has the same, or functionally equivalent, epitope specificity as the monoclonal antibody of the invention. Screening of human monoclonal antibodies of the invention, can be also carried out by utilizing CCR4 and determining whether the test monoclonal antibody is able to neutralize CCR4.

Various procedures known within the art may be used for the production of polyclonal or monoclonal antibodies directed against a protein of the invention, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "mAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice,* Academic Press, (1986) pp. 59-103) Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice,* Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of CCR4 in a sample. The antibody can also be used to try to bind to and disrupt a CCR4 activity.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may also refer to bi-specific antibodies, wherein a bi-specific antibody is composed of, for example, two covalently joined single chain antibodies, or scFvs, or two covalently joined variable heavy chain-variable light chain dimers from two antibodies that recognize different antigens.

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$ and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun 133:1335-2549 (1984); Jansen et al., Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxy-sulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments, mutations are introduced to the constant regions of the mAb such that the antibody dependent cell-mediated cytotoxicity (ADCC) activity of the mAb is altered. For example, the mutation is an LALA mutation in the CH2 domain, wherein the leucines at positions 234 and 235 of the Fc region is mutated to alanine, and abrogates binding by specific Fc receptors. In one aspect, the mAb contains mutations on one scFv molecule of the heterodimeric mAb, which reduces the ADCC activity. In another aspect, the mAb contains mutations on both chains of the heterodimeric mAb, which completely ablates the ADCC activity. For example, the mutations introduced one or both scFv molecules of the mAb are LALA mutations in the CH2 domain. These mAbs with variable ADCC activity can be optimized such that the mAbs exhibits maximal selective killing towards cells that express one antigen that is recognized by the mAb, however exhibits minimal killing towards the second antigen that is recognized by the mAb.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against CCR4

Methods for the screening of antibodies that possess the desired specificity include, but are not limited to, enzyme linked immunosorbent assay (ELISA) and other immunologically mediated techniques known within the art.

Antibodies directed against a CCR4 protein (or a fragment thereof) may be used in methods known within the art relating to the localization and/or quantitation of a CCR4 protein (e.g., for use in measuring levels of the CCR4 protein within appropriate physiological samples, for use in diagnostic methods, for use in imaging the protein, and the like). In a given embodiment, antibodies specific to a CCR4 protein, or derivative, fragment, analog or homolog thereof, that contain the antibody derived antigen binding domain, are utilized as pharmacologically active compounds (referred to hereinafter as "Therapeutics").

An antibody specific for a CCR4 protein of the invention can be used to isolate a CCR4 polypeptide by standard techniques, such as immunoaffinity, chromatography or immunoprecipitation. Antibodies directed against a CCR4 protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Antibodies of the invention, including polyclonal, monoclonal, humanized and fully human antibodies, may used as therapeutic agents. Such agents will generally be employed to treat or prevent cancer in a subject, increase vaccine efficiency or augment a natural immune response. An antibody preparation, preferably one having high specificity and high affinity for its target antigen, is administered to the subject and will generally have an effect due to its binding with the target. Administration of the antibody may abrogate or inhibit or interfere with an activity of the CCR4 protein.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding a CCR4 protein or a fragment thereof of the invention, as well as other molecules identified by the screening assays disclosed herein, can be administered for the treatment of cancer or other proliferative disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of CCR4 (or a protein or a protein fragment thereof) in a sample. Preferably, the antibody contains a detectable label. Antibodies can be polyclonal, or more preferably, monoclonal. An intact antibody, or a fragment thereof (e.g., $F_{ab}$, scFv, or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA includes Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with a CCR4 activity. Also provided are methods of identifying compounds useful to treat cancer. The invention also encompasses compounds identified using the screening assays described herein.

For example, the invention provides assays for screening candidate or test compounds which modulate the CCR4 carbonic anhydrase activity. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233,409.).

In one embodiment, a candidate compound is introduced to an antibody-antigen complex and determining whether the candidate compound disrupts the antibody-antigen complex, wherein a disruption of this complex indicates that the candidate compound modulates an CCR4 activity.

In another embodiment, at least one CCR4 protein is provided, which is exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat cancer or a proliferative disease or disorder, particularly a renal proliferative disorder.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a CCR4 neutralizing antibody. Additionally, the antigen may be a CCR4 protein or a portion thereof (e.g., the CA domain).

The screening methods disclosed herein may be performed as a cell-based assay or as a cell-free assay. In the case of cell-free assays comprising the membrane-bound forms of the CCR4 proteins, it may be desirable to utilize a solubilizing agent such that the membrane-bound form of the proteins is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton° X-100, Triton° X-114, Thesit®, Isotridecypoly(ethylene glycol ether),,, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody or the antigen (e.g. the CCR4 protein or the CA domain thereof) can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention can be detected by appropriate assays, e.g., conventional types of immunoassays. For example, a sandwich assay can be performed in which a CCR4 protein or fragment thereof (e.g., the CA domain) is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide is subsequently incubated with a second, labeled antibody or antibody bound to a coupling agent such as biotin or avidin. This second antibody may be another anti-CCR4 antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

The anti-CCR4 antibodies and scFv antibodies of the invention, when joined to a detectable moiety, provides a way for detecting "cancerous tissue" or tissue subject to aberrant cell proliferation and therefore at risk for cancer. In addition to tissue that becomes cancerous due to an in situ neoplasm, for example, the antibody-detectable moiety conjugates also provides a method of detecting cancerous metastatic tissue present in distal organs and/or tissues. Thus such tissue may be detected by contacting tissue suspected of being cancerous with the antibody-detectable moiety under appropriate conditions to cause the detectable moiety to be detected in cancerous tissue, thereby detecting the presence of cancerous tissue.

The detectable moieties can be conjugated directly to the antibodies or fragments, or indirectly by using, for example, a fluorescent secondary antibody. Direct conjugation can be accomplished by standard chemical coupling of, for example, a fluorophore to the antibody or antibody fragment, or through genetic engineering. Chimeras, or fusion proteins can be constructed which contain an antibody or antibody fragment coupled to a fluorescent or bioluminescent protein. For example, Casadei, et al., describe a method of making a vector construct capable of expressing a fusion protein of aequorin and an antibody gene in mammalian cells.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject (such as a biopsy), as well as tissues, cells and fluids present within a subject. That is, the detection method of the invention can be used to detect cancer, a cancer cell, or a cancer-associated cell (such as a stromal cell associated with a tumor or cancer cell) in a biological sample in vitro as well as in vivo. For example, in vitro techniques for detection of CCR4 include enzyme linked immunosorbent assays (ELISAs), Western blots, immunoprecipitations, and immunofluorescence. Furthermore, in vivo techniques for detection of CCR4 include introducing into a subject a labeled anti-CCR4 antibody. For example, the antibody can be labeled with a radioactive marker whose presence and location in a subject can be detected by standard imaging techniques. In embodiments, the invention provides a non-invasive method of detecting a tumor or cancer cell in a subject. The subject is administered an antibody or scFv antibody of the invention, where the antibody is linked to a detectable moiety (i.e., any moiety capable of being detected by, e.g., fluorescent, chemical, chemiluminescent, radioactive, or other means known in the art), the antibody is allowed to localize to the tumor then is detected by observation of the detectable moiety.

In the case of "targeted" conjugates, that is, conjugates which contain a targeting moiety—a molecule or feature designed to localize the conjugate within a subject or animal at a particular site or sites, localization refers to a state when an equilibrium between bound, "localized", and unbound, "free" entities within a subject has been essentially achieved. The rate at which such equilibrium is achieved depends upon the route of administration. For example, a conjugate administered by intravenous injection to localize thrombi may achieve localization, or accumulation at the thrombi, within minutes of injection. On the other hand, a conjugate administered orally to localize an infection in the intestine may take hours to achieve localization. Alternatively, localization may simply refer to the location of the entity within the subject or animal at selected time periods after the entity is administered. By way of another example, localization is achieved when a moiety becomes distributed following administration.

In all of the above cases, a reasonable estimate of the time to achieve localization may be made by one skilled in the art. Furthermore, the state of localization as a function of time may be followed by imaging the detectable moiety (e.g., a light-emitting conjugate) according to the methods of the invention, such as with a photodetector device. The "photodetector device" used should have a high enough sensitivity to enable the imaging of faint light from within a mammal in a reasonable amount of time, and to use the signal from such a device to construct an image.

In cases where it is possible to use light-generating moieties which are extremely bright, and/or to detect light-generating fusion proteins localized near the surface of the subject or animal being imaged, a pair of "night-vision" goggles or a standard high-sensitivity video camera, such as a Silicon Intensified Tube (SIT) camera (e.g., from Hammamatsu Photonic Systems, Bridgewater, N.J.), may be used. More typically, however, a more sensitive method of light detection is required.

In extremely low light levels the photon flux per unit area becomes so low that the scene being imaged no longer appears continuous. Instead, it is represented by individual photons which are both temporally and spatially distinct form one another. Viewed on a monitor, such an image appears as scintillating points of light, each representing a single detected photon. By accumulating these detected photons in a digital image processor over time, an image can be acquired and constructed. In contrast to conventional cameras where the signal at each image point is assigned an intensity value, in photon counting imaging the amplitude of the signal carries no significance. The objective is to simply detect the presence of a signal (photon) and to count the occurrence of the signal with respect to its position over time.

At least two types of photodetector devices, described below, can detect individual photons and generate a signal which can be analyzed by an image processor. Reduced-Noise Photodetection devices achieve sensitivity by reducing the background noise in the photon detector, as opposed to amplifying the photon signal. Noise is reduced primarily by cooling the detector array. The devices include charge coupled device (CCD) cameras referred to as "backthinned", cooled CCD cameras. In the more sensitive instruments, the cooling is achieved using, for example, liquid nitrogen, which brings the temperature of the CCD array to approximately −120° C. "Backthinned" refers to an ultra-thin backplate that reduces the path length that a photon follows to be detected, thereby increasing the quantum efficiency. A particularly sensitive backthinned cryogenic CCD camera is the "TECH 512", a series 200 camera available from Photometrics, Ltd. (Tucson, Ariz.).

"Photon amplification devices" amplify photons before they hit the detection screen. This class includes CCD cameras with intensifiers, such as microchannel intensifiers. A microchannel intensifier typically contains a metal array of channels perpendicular to and co-extensive with the detection screen of the camera. The microchannel array is placed between the sample, subject, or animal to be imaged, and the camera. Most of the photons entering the channels of the array contact a side of a channel before exiting. A voltage applied across the array results in the release of many electrons from each photon collision. The electrons from such a collision exit their channel of origin in a "shotgun" pattern, and are detected by the camera.

Even greater sensitivity can be achieved by placing intensifying microchannel arrays in series, so that electrons generated in the first stage in turn result in an amplified signal of electrons at the second stage. Increases in sensitivity, however, are achieved at the expense of spatial resolution, which decreases with each additional stage of amplification. An exemplary microchannel intensifier-based single-photon detection device is the C2400 series, available from Hamamatsu.

Image processors process signals generated by photodetector devices which count photons in order to construct an image which can be, for example, displayed on a monitor or printed on a video printer. Such image processors are typically sold as part of systems which include the sensitive photon-counting cameras described above, and accordingly, are available from the same sources. The image processors are usually connected to a personal computer, such as an IBM-compatible PC or an Apple Macintosh (Apple Computer, Cupertino, Calif.), which may or may not be included as part of a purchased imaging system. Once the images are in the form of digital files, they can be manipulated by a variety of image processing programs (such as "ADOBE PHOTOSHOP", Adobe Systems, Adobe Systems, Mt. View, Calif.) and printed.

In one embodiment, the biological sample contains protein molecules from the test subject. One preferred biological sample is a peripheral blood leukocyte sample isolated by conventional means from a subject.

The invention also encompasses kits for detecting the presence of CCR4 or a CCR4-expressing cell in a biological sample. For example, the kit can comprise: a labeled compound or agent capable of detecting a cancer or tumor cell (e.g., an anti-CCR4 scFv or monoclonal antibody) in a biological sample; means for determining the amount of CCR4 in the sample; and means for comparing the amount of CCR4 in the sample with a standard. The standard is, in some embodiments, a non-cancer cell or cell extract thereof. The compound or agent can be packaged in a suitable container. The kit can further comprise instructions for using the kit to detect cancer in a sample.

Bi-Specific Antibodies

A bi-specific antibody (bsAb) is an antibody comprising two variable domains or scFv units such that the resulting antibody recognizes two different antigens. The present invention provides for bi-specific antibodies that recognize CCR4 and a second antigen. Exemplary second antigens include tumor associated antigens, cytokines and cell surface receptors. In some embodiments, the second antigen can be CAIX (carbonic anhydrase IX, or G250, PD-L1, IL21, IL21R, HVEM, CD160, TIM3 or GAL9.

A bi-specific antibody of the present invention comprises a heavy chain and a light chain combination or scFv of the CCR4-IgG4 antibody disclosed herein.

Bi-specific antibodies of the present invention can be constructed using methods known art. In some embodiments, the bi-specific antibody is a single polypeptide wherein two different heavy-light chain heterodimers or two different scFv antibodies, or fragments thereof, that each recognize a different antigen are joined by a long linker polypeptide, of sufficient length to allow intramolecular association between the two scFv molecules to form a bi-specific antibody, with two heavy chains and two light chains. In one embodiment, one of the scFv molecules recognizes CCR4, for example, any of the scFv antibodies described herein. In other embodiments, the bi-specific antibody consists of more than one polypeptide, for example, two separate scFv antibodies, or fragments thereof, linked by covalent or non-covalent bonds, wherein one of the scFv antibodies recognizes CCR4.

In one embodiment, the bi-specific antibody is constructed using the "knob into hole" method (Ridgway et al., Protein Eng 7:617-621 (1996)). In this method, the Ig heavy chains of the two different variable domains are reduced to selectively break the heavy chain pairing while retaining the heavy-light chain pairing. The two heavy-light chain heterodimers that recognize two different antigens are mixed to promote heteroligation pairing, which is mediated through the engineered "knob into holes" of the CH3 domains.

In another embodiment, the bi-specific antibody can be constructed through exchange of heavy-light chain heterodimers from two or more different antibodies to generate a hybrid antibody where the first heavy-light chain heterodimer recognizes CCR4 and the second heavy-light chain heterodimer recognizes a second antigen. The mechanism for generating a bi-specific antibody consisting of two heavy-light chain heterodimers from two different antibodies is similar to the formation of human IgG4, which also functions as a bispecific molecule. Dimerization of IgG heavy chains is driven by intramolecular force, such as the pairing the CH3 domain of each heavy chain and disulfide bridges. Presence of a specific amino acid in the CH3 domain (R409) has been shown to promote dimer exchange and construction of the IgG4 molecules. Heavy chain pairing is also stabilized further by interheavy chain disulfide bridges in the hinge region of the antibody. Specifically, in IgG4, the hinge region contains the amino acid sequence Cys-Pro-Ser-Cys (in comparison to the stable IgG1 hinge region which contains the sequence Cys-Pro-Pro-Cys) at amino acids 226-230. This sequence difference of Serine at position 229 has been linked to the tendency of IgG4 to form novel intrachain disulfides in the hinge region (Van der Neut Kolfschoten, M. et al., 2007, Science 317:1554-1557 and Labrijn, A. F. et al, 2011, Journal of immunol 187:3238-3246).

In another embodiment, the use of glutathione and glutathione disulfide can be used in the production of bi-specific antibodies from two distinct full antibodies. For example, the full antibodies, each which recognize different antigens, are incubated with reducing glutathione to separate the antibodies into heavy-light chain heterodimers, or molecules. The heavy-light chain heterodimers may be mixed with oxidized glutathione (GSSG) which allows reassembly and reoxidation to form highly pure bi-specific antibodies.

Therefore, bi-specific antibodies of the present invention can be created through introduction of the R409 residue in the CH3 domain and the Cys-Pro-Ser-Cys sequence in the hinge region of antibodies that recognize CCR4 or a second antigen, so that the heavy-light chain dimers exchange to produce an antibody molecule with one heavy-light chain dimer recognizing CCR4 and the second heavy-light chain dimer recognizing a second antigen, wherein the second antigen is any antigen disclosed herein. Heavy-light chain heterodimer exchange can also be enhanced with addition of a reducing agent, such as reduced glutathione, to promote the exchange. Known IgG4 molecules may also be altered such that the heavy and light chains recognize CCR4 or a second antigen, as disclosed herein. Use of this method for constructing the bi-specific antibodies of the present invention may be beneficial due to the intrinsic characteristic of IgG4 molecules wherein the Fc region differs from other IgG subtypes in that it interacts poorly with effector systems of the immune response, such as complement and Fc receptors expressed by certain white blood cells. This specific property makes these IgG4-based bi-specific antibodies attractive for therapeutic applications, in which the antibody is required to bind the target(s) and functionally alter the signaling pathways associated with the target(s), however not trigger effector activities.

In some embodiments, mutations are introduced to the constant regions of the bsAb such that the antibody dependent cell-mediated cytotoxicity (ADCC) activity of the bsAb is altered. For example, the mutation is an LALA mutation in the CH2 domain, wherein the leucines at positions 234 and 235 of the Fc region is mutated to alanine, and abrogates binding by specific Fc receptors. In one aspect, the bsAb contains mutations on one scFv molecule of the heterodimeric bsAb, which reduces the ADCC activity. In another aspect, the bsAb contains mutations on both chains of the heterodimeric bsAb, which completely ablates the ADCC activity. For example, the mutations introduced one or both scFv molecules of the bsAb are LALA mutations in the CH2 domain. These bsAbs with variable ADCC activity can be optimized such that the bsAbs exhibits maximal selective killing towards cells that express one antigen that is recognized by the bsAb, however exhibits minimal killing towards the second antigen that is recognized by the bsAb.

The present invention provides for bi-specific antibodies that recognize CCR and a second antigen. In one embodiment, the second antigen is PD-L1. In another embodiment, the second antigen is CAIX. In other embodiments the second antigen is CA-IX, PD-L1, IL21, IL21R, HVEM, CD160, TIM3, GITR, LAG3 or GAL9.

The bi-specific antibodies disclosed herein may be useful in treatment of diseases or medical conditions, for example, cancer. The cancer is, for example, a solid cancer, such as renal cell carcinoma, breast cancer or prostate cancer. In other embodiments, the cancer is a cancer in which CAIX, PD-L1 or HVEM is overexpressed when compared to tissue or a subject that does not have cancer. The bi-specific antibodies of the present invention may be used to treat, prevent, or alleviate a symptom of the cancer.

The bi-specific antibodies of the present invention may be used to increase T cell proliferation, in which the T cell is a regulatory T cell. The bi-specific antibodies of the present invention may be particularly useful for promoting or augmenting a T cell response, such as an antigen-specific T cell response. The bi-specific antibodies of the present invention can also be useful for reversing regulatory T cell-mediated suppression of effector T cell proliferation.

Fusion Proteins

The invention provides a fusion protein containing a CCR4-IgG4 antibody disclosed herein, or a functional fragment thereof, operably linked to a second protein. The second protein can be, for example, a cytokine or a growth factor. In particularly preferred embodiments, the cytokine is IL-2 or TGF-beta. In some other embodiments, the second protein may be a therapeutic agent, such as a toxin, or a detectable moiety, such as a fluorescent protein for detection. In some embodiments, the CCR4-IgG4 antibodies of the present invention may be operably linked to more than one additional protein or peptide, for example 2, 3, 4, 5, 6, 7, 8, 9, or 10 additional proteins or peptide sequences.

In some embodiments, the CCR4-IgG4 antibody disclosed herein, or functional fragment thereof, is joined directly to the second protein. In other embodiments, the CCR4-IgG4 antibody, or functional fragment thereof, is joined to the second protein via a linker, such as a flexible polypeptide chain. The linker can be any suitable linker of any length, but can be at least 1, 2, 3, 4, 5, 10, 15, 20, 25, or 30 amino acids in length. In one embodiment, the linker is an amino acid sequence that is naturally present in immunoglobulin molecules of the host, such that the presence of the linker would not result in an immune response against the linker sequence by the mammal. Fusion proteins of the present invention that include more than one additional protein to the CCR4-IgG4 antibody may have multiple linker sequences that join each additional protein or peptide sequence.

The fusion proteins of the present invention may be constructed by recombinant methods known to the skilled artisan. For example, an expression vector containing the nucleic acid sequence encoding a CCR4-IgG4 antibody of the present invention can be operably linked to the nucleic acid sequence encoding the second protein and can be introduced to an expression system to translate and produce the fusion protein. Alternatively, one skilled in the art could readily utilize de novo protein synthesis techniques to produce the fusion proteins described herein.

Methods of Treatment

The invention provides for both prophylactic and therapeutic methods of treating a subject at risk of (or susceptible to) a cancer, or other cell proliferation-related diseases or disorders. Such diseases or disorders include but are not limited to, e.g., those diseases or disorders associated with aberrant expression of CCR4. For example, the methods are used to treat, prevent or alleviate a symptom of a hematologic cancer such cutaneous T-cell Lymphoma (CTCL), mycosis fungoides (MF), primary cutaneous anaplastic large cell Lymphoma (cutaneous ALCL), Sezary syndrome, or adult T cell Leukemia/Lymphoma (ATLL). Alternatively, the methods are used to treat, prevent or alleviate a symptom of a solid tumor such as renal cell carcinoma, breast cancer, lung cancer, ovarian cancer, prostate cancer, colon cancer, cervical cancer, brain cancer, liver cancer, pancreatic cancer or stomach cancer. In other embodiments, the antibodies of the present invention, such as bi-specific antibodies of the present invention, can be used for the treatment of cancers that are characterized by CAIX, PD-L1, HVEM-overexpressing tumors. For example, the bi-specific antibody that recognizes CAIX and CCR4 may be used for treatment of a cancer with tumors that overexpress CAIX. For example, the bi-specific antibody that recognizes PD-L1 and CCR4 may be used for treatment of a cancer with tumors that overexpress PD-L1. For example, the bi-specific antibody that recognizes HVEM and CCR4 may be used for treatment of a cancer with tumors that overexpress HVEM.

Accordingly, in one aspect, the invention provides methods for preventing, treating or alleviating a symptom cancer or a cell proliferative disease or disorder in a subject by administering to the subject a monoclonal antibody or scFv antibody of the invention. For example, a CCR4-IgG4 antibody may be administered in therapeutically effective amounts.

Subjects at risk for cancer or cell proliferation-related diseases or disorders include patients who have a family history of cancer or a subject exposed to a known or suspected cancer-causing agent. Administration of a prophylactic agent can occur prior to the manifestation of cancer such that the disease is prevented or, alternatively, delayed in its progression.

In another aspect, tumor cell growth is inhibited or suppressor T-cell activity is decreased by contacting a cell with a CCR4 antibody of the invention. The cell is any cell that expresses CCR4. For example the cell is T-cell.

Also included in the invention are methods of increasing or enhancing an immune response to an antigen. An immune response is increased or enhanced by administering to the subject a monoclonal antibody or scFv antibody of the invention. The antigen is a viral (e.g. HIV), bacterial, fungal or tumor antigen. The immune response is a natural immune response. By natural immune response is meant an immune response that is a result of an infection. The infection is a chronic infection.

Alternatively, the immune response is a response induced due to a vaccination. Accordingly, in another aspect the invention provides a method of increasing vaccine efficiency by administering to the subject a monoclonal antibody or scFv antibody of the invention and a vaccine. The antibody and the vaccine are administered sequentially or concurrently. The vaccine is a tumor vaccine a bacterial vaccine or a viral vaccine.

The immune response is augmented for example by augmenting antigen specific T effector function.

Combinatory Methods

The invention provides treating cancer in a patient by administering two antibodies that bind to the same epitope of the CCR4 protein or, alternatively, two different epitopes of the CCR4 protein. Also, the cancer is treated by administering a first antibody that binds to CCR4 and a second antibody that binds to a protein other than CCR4.

Additionally, the invention provides administration of an antibody that binds to the CCR4 protein and an anti-neoplastic agent, such a small molecule, a growth factor, a cytokine or other therapeutics including biomolecules such as peptides, peptidomimetics, peptoids, polynucleotides, lipid-derived mediators, small biogenic amines, hormones, neuropeptides, and proteases. Small molecules include, but are not limited to, inorganic molecules and small organic molecules. Suitable growth factors or cytokines include an IL-2, GM-CSF, IL-12, and TNF-alpha. Small molecule libraries are known in the art. (See, Lam, Anticancer Drug Des., 12:145, 1997.)

The invention will be further described in the following examples, which do not limit the scope of the invention described in the claims.

EXAMPLES

Example 1

General Methods

Antibodies and Flow Cytometry Analysis

IgG and scFv-Fcs format of mAb2-3 and KM2760 were constructed by cloning the single-chain variable region (scFv) into pcDNA3.1-Hinge vector in frame with human IgG1 Fc region and by cloning heavy-chain variable region (VH) and light-chain variable region (VL) into TCAE5.3 vector. For IgG4 cloning, the cDNA sequence of immunoglobulin heavy constant gamma 4 was from GenBank: BC111019.1 and used to replace the IgG1 Fc region in TCAE5.3 constructing mAb2-3 IgG4. Similarly, stabilized form of IgG4 (see additional data) have also been constructed (see new ref). Antibodies were produced in 293T or 293F cells and purified by proteinA-Sepharose (Amersham) affinity chromatography.

Chemotaxis

Treg cells were placed in Transwell-migration wells (5 µM pore; Corning) with or without mAb2-3 IgG1 or mAb2-3 IgG4 for 3 h at 37° C., and migrated cells harvested from the bottom chamber containing conditioned medium from either IGROV-1, OVCAR-5 or OVCAR-8 cells. Percentages of migrated cells were calculated by dividing the number of transmigrated Treg by the number of input cells. Human CD4+ T cells were isolated by CD4+ T cell isolation kit (Miltenyi Biotech) and placed in Transwell-migration assays with mAb2-3 IgG1 or mAb2-3 IgG4 for 3 h at 37° C., and migrated cells (CD4+CD25high) were enumerated as above in response to conditioned medium from either IGROV-1, OVCAR-5 or OVCAR-8 cells. Percentages of migrated cells were calculated by dividing the number of transmigrated CD4+CD25high cells by the number of input cells with comparable CD4+ and CD25+ levels.

Antibody-Dependent Cell Cytotoxicity Assay

ADCC assays were performed using the LDH release assay method. Briefly, SCID/Beige mouse neutrophils, human PBMCs, or purified human NK cells and neutrophils were used as effector cells and Mac-1, Cf2Th-CCR4, or Cf2Th cells were used as target cells. Target cells were plated at a density of $1 \times 10^4$ cells/well into 96-well plates and then antibodies were added at an appropriate concentration. After one-hour incubation, fresh effector cells were added to achieve an appropriate E/T ratio. After incubation at 37° C. (PBMCs for 4 hours, NK cells for 16 hours and neutrophils for 6 hours), the supernatants from each well were recovered by centrifugation at 300×g for 5 min. The supernatant were measured using a nonradioactive cytotoxicity assay kit (Promega, WIS.). The absorbance at 490 nm of the plates was determined using an ELISA reader. For 51Cr release assay, $1 \times 106$ Mac-1 cells were labeled with 100 µCi (3.7 MBq) of Na51Cr (Amersham International) for 1 h at 37° C., washed extensively, and used as targets. 51Cr-labeled target cells (5000 per well) were seeded into 96-well plates. Experiments were conducted in triplicates at various PBMC (effector) to Mac-1 (target) ratios of 12.5:1, 25:1, and 50:1, incubated at 37° C. for 4 hours, and then the release of 51Cr into supernatants was determined. The cytotoxicity was calculated by the following formula:

% Cytotoxicity=$100 \times (E-SE-ST)/(M-ST)$ where E is the experimental release of the LDH form the target cells incubated with effector cells and antibody, SE the spontaneous release of the LDH from the effector cells, ST the spontaneous release of the LDH from the target cells and M is the maximum release of the LDH from the target cells incubated with 10% triton-X.

Regulatory T Cell Suppression Assay

CD4+CD25high and CD4+CD25– T cells were sorted by FACSCanto II flow cytometer using anti-CD4 and anti-CD25 antibodies (Biolegend). CD4+CD25-Teffs (2500 cells) were cultured with or without CD4+CD25high Tregs (2500 or 1250 cells) in round-bottom 96-well plates coated with bound anti-CD3 (0.05 µg/ml) and soluble anti-CD28 (1 µg/ml) antibodies (Biolegend, CA). 25,000 irradiated (300rad) CD3-depleted PBMCs with or without c1567IgG were added into the cocultured wells. Proliferation of T cells was measured by incorporation of 3H-thymidine on day 5 using a scintillation counter. The percent proliferation of Teffs in Tregs cocultures in all analyses was normalized to the proliferation of Teffs in mono-Teffs culture; the proliferation of mono-Teffs culture was considered 100% for this normalization. For activation, plates were coated with anti-CD3 at 37° C. for 2 hours and washed twice with PBS.

CCR4+ CTCL Tumor-Bearing Mouse Model

Human cancer xenografts were established in SCID/Beige mice (Charles River). Cells were injected subcutaneously into the dorsolateral flank in 6-week mice. After 24 hours of injection, mice were randomly assigned to different treatment groups and treated with 3 mg/kg of mAb2-3 IgG1 or mAb2-3 IgG4, and mouse IgG4 (twice a week for three weeks) or 5 mg/kg of control-scFv-Fc, c1567-scFv-Fc, h1567-scFv-Fc, and equivalent volumes of saline by i.p. injection (twice a week for four weeks). Mouse body weight and tumor size were measured and monitored twice a week using digital caliper or Xenogen imaging. The tumor volumes were calculated using the equation, length×(width)2× 0.52. Animal care was carried out in accordance with the guidelines of Animal Care and Use Committee of Dana-Farber Cancer Institute.

Statistical Analyses

Data was analyzed using two-sided unpaired Student's t-test. We considered a P value below 0.05 as significant for all analyses. All values are represented as mean±standard deviation (S.D)

Statistical analyses were performed using 2-way ANOVA with Bonferroni post hoc tests and unpaired 2-tailed t-tests using GraphPad Prism 5 (GraphPad Software, Inc., La Jolla, Calif.). P values less than 0.05 were considered statistically significant.

In Vitro Antibody-Dependent Cell Cytotoxicity Assay

ADCC was performed using the lactate dehydrogenase (LDH) release assay method, according to the CytoTox96 non-radioactive cytotoxicity assay procedure specified by the manufacturer (Promega, Madison, Wis.). Mouse neutrophils purified from SCID-BEIGE mouse or purified human NK cells from PBMC was used as effector cells and CCR4+ Mac1 tumor cells were used as target cells. Briefly, purified SCID-BEIGE mouse neutrophils or NK cells were plated at a density of $1 \times 10^4$ cells per well in a round-bottom 96-well plate in the presence of h1567 or 11A minibodies. After 1-hour of incubation, freshly prepared effector cells were added at an effector-target cell ratio (E:T) of 80:1 (mouse neutrophils) or 2:1 (human NK cells). After 2 h incubation at 37° C., supernatants of each well were recovered by centrifugation at 300×g for 5 min. LDH activity in the supernatant was determined by measuring absorbance at a wavelength of 490 nm. The cytotoxicity (%) was calculated according to the following formula:

% Cytotoxicity=$100 \times (E-SE-ST)/(M-ST)$ where E is the LDH release by effector-target coculture, SE the spontaneous release of the LDH from the effector cells, ST the spontaneous release of the LDH from the target cells and M the maximum release of the LDH from the target cells incubated with lysis solution (10% Triton-X). All measurements were done in triplicate.

Example 2

In Vitro Treg Chemoattraction Mediated by CLL2 is Inhibited by mAB2-3 IgG4 in a Dose Dependent Manner The ovarian cancer cell lines IGROV-1, OVCAR-5, and OVCAR-8 were assayed for expression of the CCR4 ligand, CCL22 by FACS. All ovarian cancer cell lines had appreciable levels of CCL22 expression, with the exception of OVCAR-8. Cell culture supernatant from each of the three cancer cell lines was used for chemoattraction assays. Specifically, transwell assays were performed to assess the migration of CD4+/CD25+ Treg cells to the bottom chamber of the transwell which contained supernatant from one of the three ovarian cancer cell lines. Tregs incubated in transwells that had ovarian cancer cell conditioned medium resulted in 100% migration of the cells to the bottom chamber. In contrast, transwell assays in which the bottom chamber contained fresh culture medium resulted in less than 40% migration of the Treg to the bottom chamber. Addition of either, mAb2-3 IgG1, or mAb2-3 IgG4 resulted in a statistically significant reduction in the migration of Tregs to the bottom chamber when the bottom chamber contained supernatant from IGROV-1 cells or OVCAR-5 cells. (See FIG. 1A-B).

Figure 3:
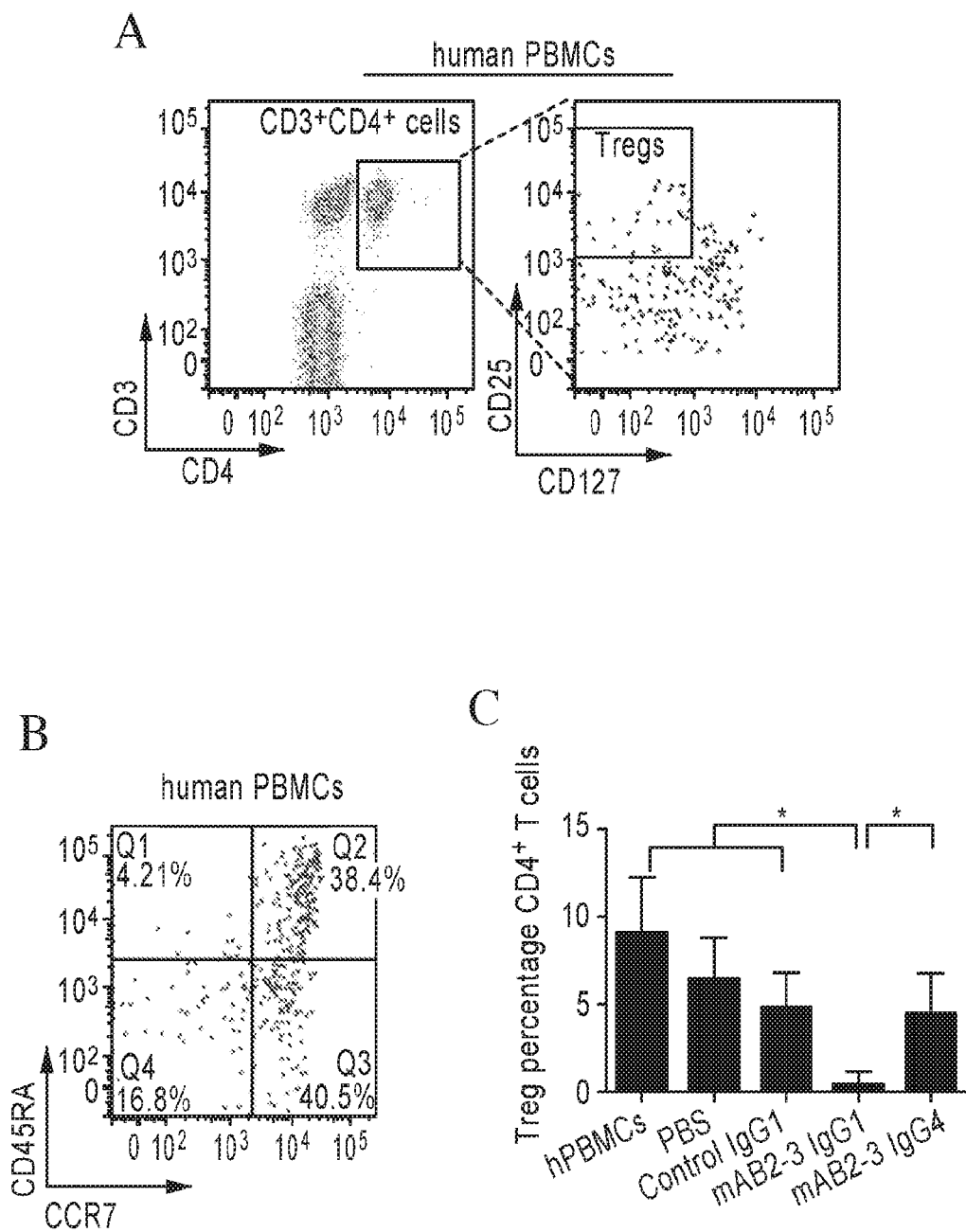
FIG. 3. Validation of human PBMCs distribution in vivo. The FACS plots and graphs in (A) and (B) depict the measurement of the CD4+ T cell population after in vivo treatment with anti-CCR4 antibodies. First, mice were received $1 \times 10^7$ human PBMCs through tail vein and then 3 mg/kg of antibodies were injected intravenously into mice. After a 24 hour circulation period in vivo, mouse blood was collected and human PBMCs were stained with Pacific blue conjugated anti-CD3, Brilliant Violet conjugated anti-CD4, APC conjugated anti-CD25, PE-Cy7 conjugated anti-CD127, PE-Cy5 conjugated anti-CD45RA, and PerCp-Cy5 conjugated anti-CCR7 antibodies, and gated to distinguish Tregs, Tcms, Tems, Teffs, and Tnaives. (C) The percentage of CD25+CD127− Treg, (D) CD45RA+CCR7− Teff, (E) CD45RA+CCR7+ Tnaive, (F) CD45RA-CCR7− Tem, and (G) CD45RA-CCR7+ Tcm population in CD3+CD4+ T cells are shown from the average of three independent experiments. *, p value<0.05. (H) Quantification of in vivo T cell population after antibody treatment. *, p value<0.05. In this experiment, mAb2-3 IgG1 mediated Treg depletion and decreased naïve T cell population. In the contrast, the IgG4 format of mAb2-3 lost the depletion activity on T cells and maintains the normal T cell subpopulations in vivo.
Figure 3:
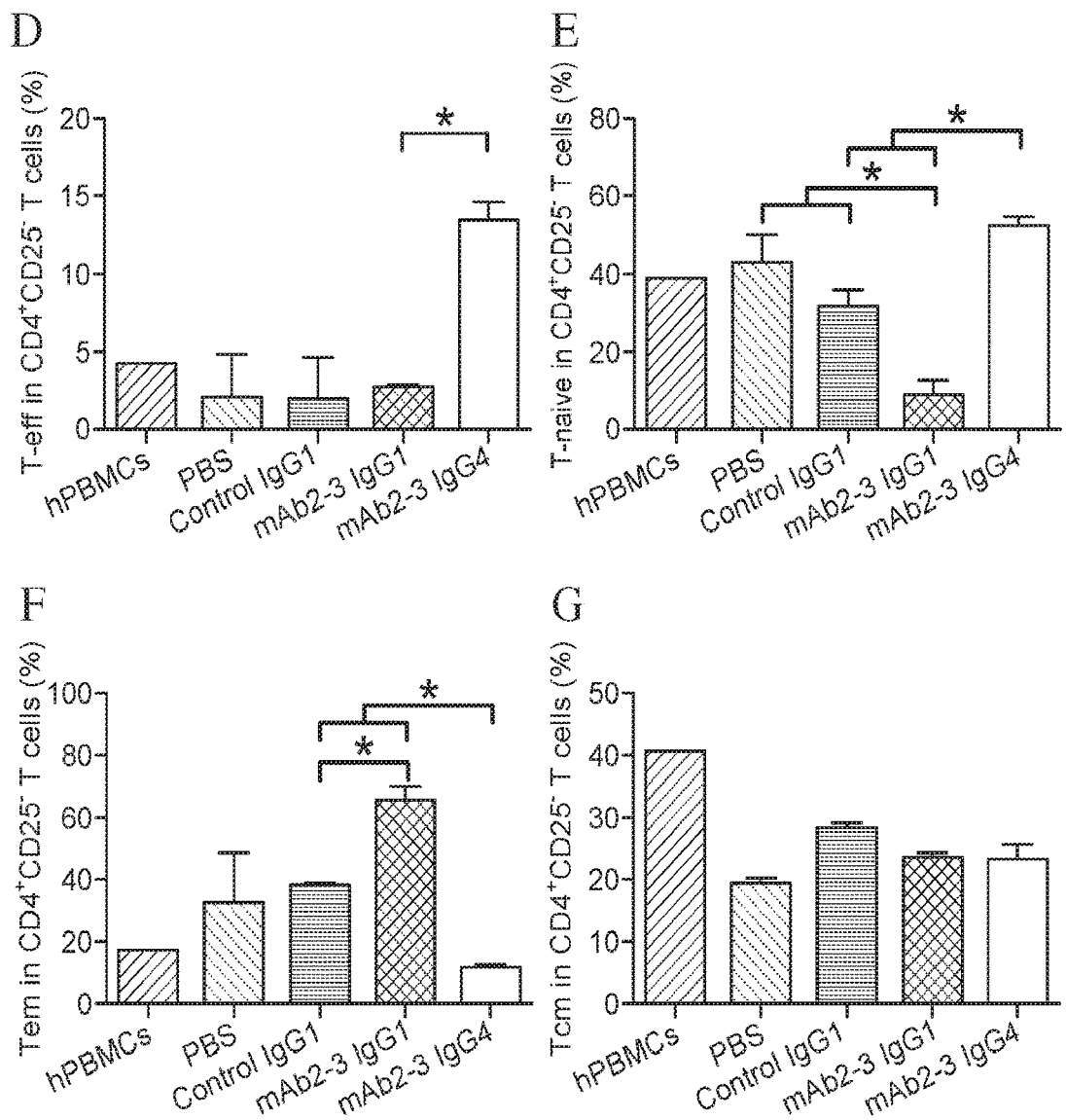

The effect of mAb2-3 IgG4 dosage on the ability to inhibit the migration of human lymphocytes to the bottom chamber of a transwell containing CCL22 rich medium demonstrates that 0.8 µg/ml results in a decrease in the migration of human lymphocytes by greater than 50% to the bottom chamber, whereas addition of 20 µg/ml results in a near complete inhibition of transwell migration. (See FIG. 3B).

Example 3

In Vivo Treg Chemoattraction Mediated by CLL2 is Inhibited by mAB2-3 IgG4

Figure 2:
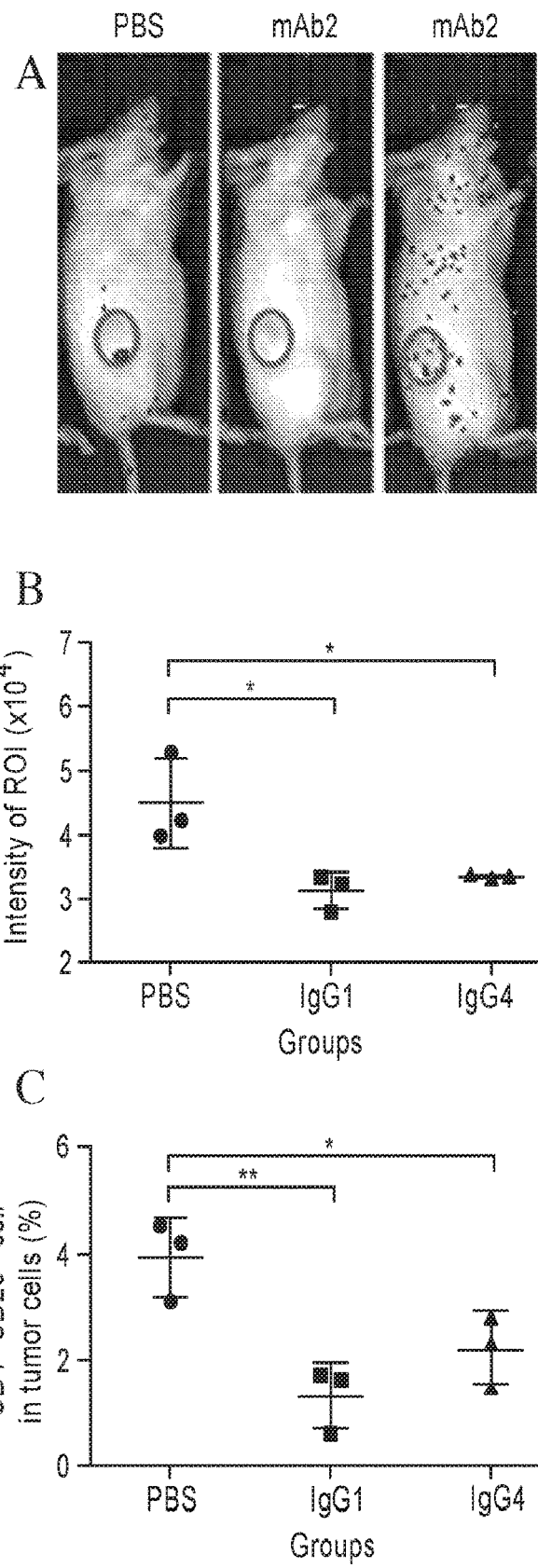
FIG. 2. In vivo Chemoattraction of human lymphocytes by CCL22-secreting IGROV-1 xenograft is inhibited by mAb2-3. (A) Mice bearing ovarian tumor cells were injected with luciferized CD4+CD25+CD127dim/− Treg cells and treated with of 3 mg/kg of mAb2-3 IgG1 or IgG4 or an equal volume of PBS. The in vivo bioluminescence images of the ovarian cancer xenograft mouse model at 18 hours (imaging) post-injection of luciferized CD4+CD25+CD127dim/− T cells. (B) The bioluminescence intensity of tumor region was measured by IVIS imaging system and software. (C) Tumors were harvested and treated with collagenase, stained with anti-CD4 and anti-CD25 antibodies, and then analyzed by flow cytometry. The percentage of CD4+CD25+ Tregs is shown. Statistical values were computed with Student's t-test. * and **, represent p value<0.5 and 0.01, respectively.

INGROV-1 cells were injected subcutaneously into the dorsolateral flank of immunocompromised mice, followed by a period of growth. Mice subsequently received a tail vein injection of Treg cells labeled with luciferase (CD4+/CD25+/CD127dim/−). These mice were then treated with either 3mg/kg mAb2-3 IgG1, 3mg/kg mAb2-3 IgG4, or equal volume of PBS as a control, in order to assess the migration of the labeled Tregs to the site of the tumor. In vivo bioluminescence assays demonstrated that the migration of Tregs to the tumor area was lessened following the administration of either mAb2-3 IgG1 or mAb2-3 IgG4. (See FIG. 2).

Example 4 mAb2-3 IgG4 Does Not Result in Lymphocyte Depletion

Human peripheral blood mononuclear cells (PBMCs) were injected via tail vein into immunocompromised mice and allowed to incorporate into the circulation. Mice were subsequently administered either mAb2-3 IgG1 or mAb2-3 IgG4, followed by a 24 hour rest period prior to analysis of the PBMCs. Blood was collected and the amounts of human derived Tregs were assessed by FACS analysis. The data demonstrate that following the administration of mAb2-3 IgG1, there was a significant reduction of the amount of Tregs compared to those found after administration of the PBS control. In contrast, following administration of the mAb2-3 IgG4 antibody, there was no statistically significant difference found in the amount of Tregs when comparing the amounts found following administration of PBS or a control IgG. These data demonstrate that mAb2-3 IgG4 does not deplete the amount of total Tregs in the circulation, whereas mAb2-3 IgG1 does result in Treg depletion.

Characterization of other T-cell populations within the human derived PBMCs following administration revealed that there was a greater amount of T-effector cells and T-naïve cells following administration of mAb2-3 IgG4 when compared to the amounts of these cells following administration of mAb2-3 IgG1. (See FIG. 3).

Collectively these data, and the data presented in Example 3, show that mAb2-3 IgG4 modulates regulatory T-cell recruitment without inducing T lymphocyte depletion.

Example 5

Figure 4:
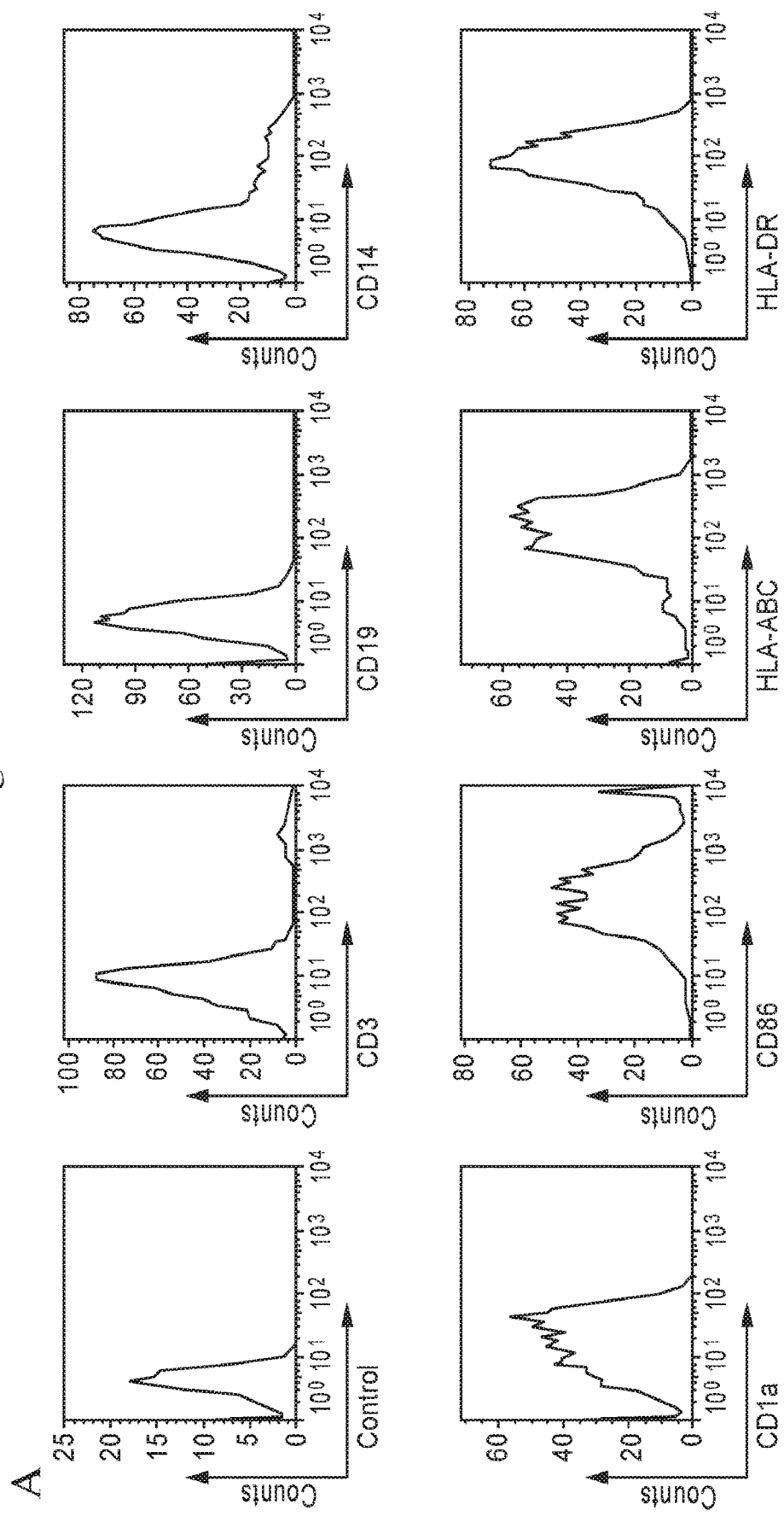
FIG. 4. Generation and verification of tumor-primed T cells to IGROV-1 ovarian cancer cells. (A) The verification of monocyte-derived dendritic cells (DCs). (B) Human tumor-primed T cells were incubated with tumor-pulsed DCs or unpulsed DCs. After a 48-hour incubation, the supernatant was harvested and IFN-gamma was measured by MSD. (C) Human tumor-primed T cells were incubated with IGROV-1 or Tregs. The supernatant was harvested, IFN-gamma was measured by MSD, (D) and the LDH was measured by ELISA to detect the cell death percentage. Results are expressed as mean±S.D. and Student's t-test.
Figure 4:
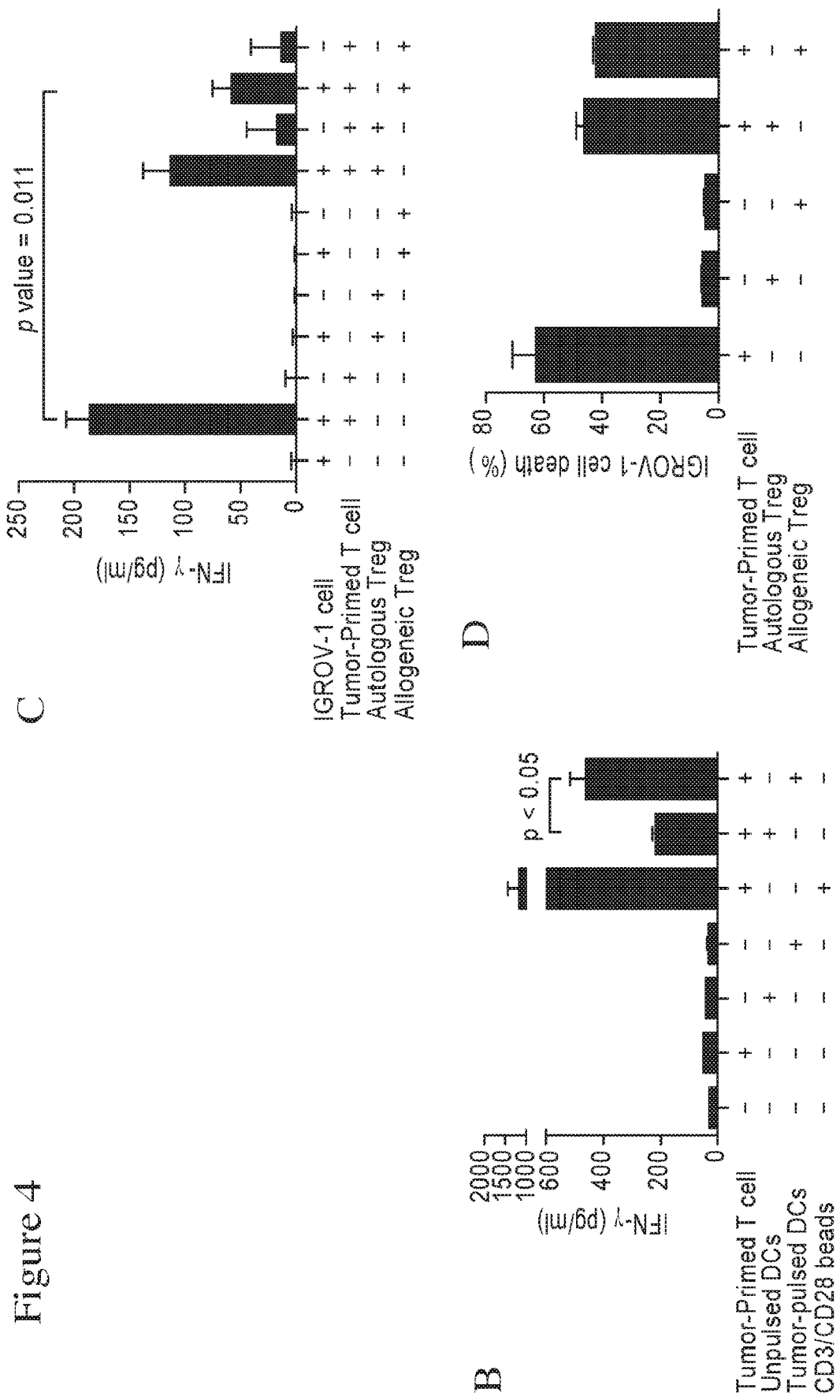

Tumor Primed T-Cells Mediate IGROV-1 Cell Death and Secrete IFN-γ Differentially in the Presence of Tregs Cells In order to assess the dynamics of IFN-γ secretion by tumor-primed T-cells, INGROV-1 tumor primed T-cells were incubated with either tumor-pulsed dendritic cells (DCs) or with unpulsed DCs, followed by measurement of IFN-γ levels in the medium. IGROV-1 tumor primed T-cells maintained high levels of IFN-γ secretion following incubation with tumor-pulsed dendritic cells (DCs) or with co-incubation with CD3/CD28 beads. In contrast, unpulsed DCs co-incubated with tumor primed T-cells, resulted in less IFN-γ secretion by the tumor primed T-cells. Additional experiments aimed to assess the influence of Treg cells on the secretion of IFN-γ by the tumor primed T-cells. These data reveal a reduction in the IFN-γ levels following incubation with either autologous or allogeneic Treg cells. (See FIG. 4B-C).

Additional in vitro studies aimed to assess the amount of IGROV-1 cell death following incubation with tumor-primed T-cells in the presence of either autologous or allogeneic Treg cells. The data indicate a reduction in the amount of IGROV-1 cell death following incubation with tumor-primed T-cells and either autologous or allogenic Treg cells, when compared with tumor-primed T-cells incubated in the absence of either Treg population. (See FIG. 4D).

Example 6

In Vivo Reduction of Tumor Size Following Administration of mAb2-3 IgG4

Figure 5:
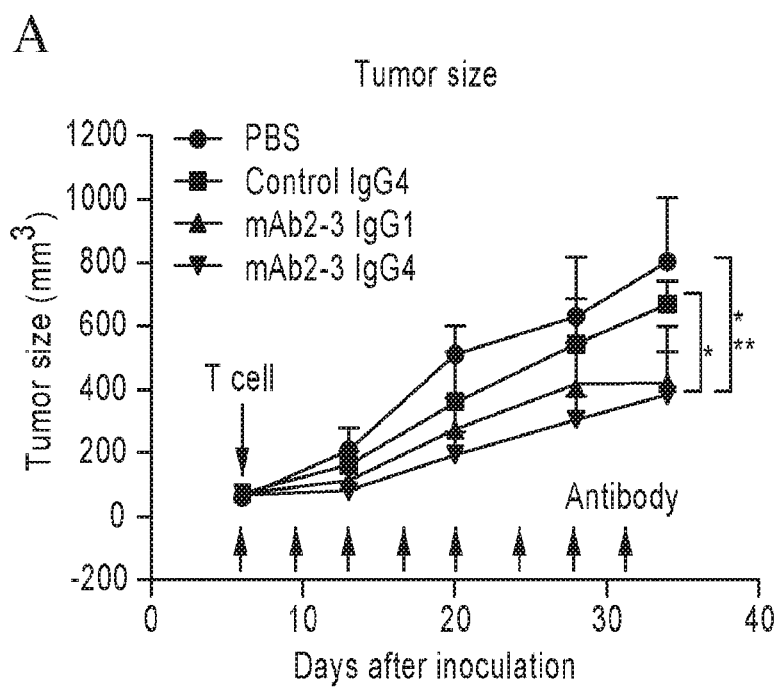
FIG. 5. Immunomodulatory therapy of mAb2-3 in IGROV-1 xenograft mice baring IGROV-1-primed T cells. (A) Mice were inoculated with $5 \times 10^6$ IGROV-1 tumor cells. When the tumor reached the size of 50 mm³, $1 \times 10^7$ IGROV- 1-primed T cells, 1×10⁶ Tregs and 1 mg/kg of antibodies were injected through tail veil. Mice were treated twice per week. Tumor sizes were calculated by caliper and measured as length x (width) 2×0.52. Grey *, p<0.05, compared to mAb2-3 IgG1; Black * and **, p<0.05 and p<0.01, compared to mAb2-3 IgG4. (B) Tumors were harvested and weighted. Bar, 1 cm. (C) Mice body weight were monitored through the entire experiment. (D) After antibody treatment, the T cell subpopulations in human T cells were measured by flow cytometry. In these NSG mice bearing tumor-primed T cells showed enhanced killing activity after treating with mAb2-3 IgG1 or IgG4. These results show that both Treg depletion and inhibition of Treg recruitment by mAb2-3 are beneficial to tumor treatment.
Figure 5:
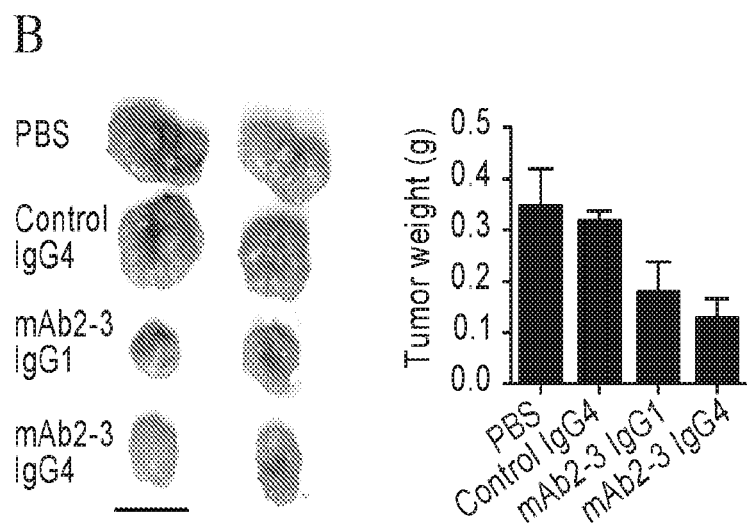
Figure 5:
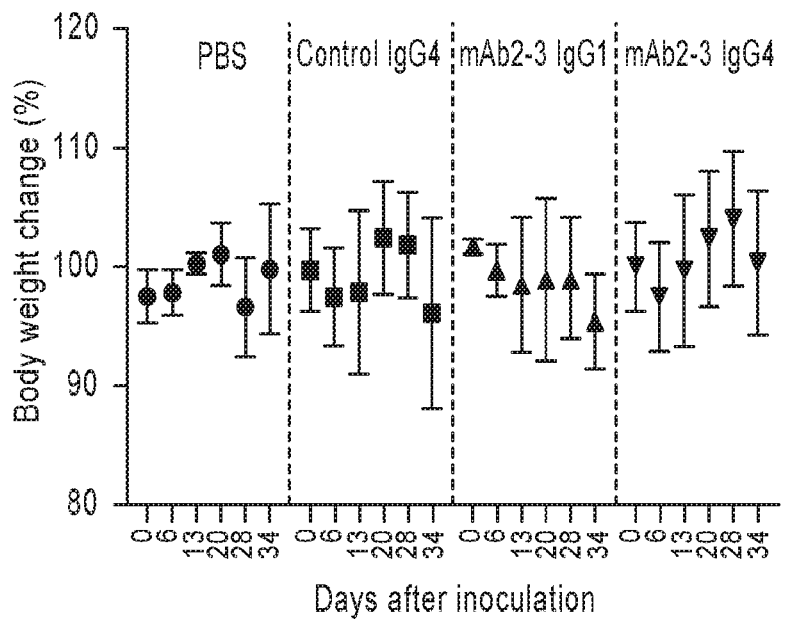
Figure 5:
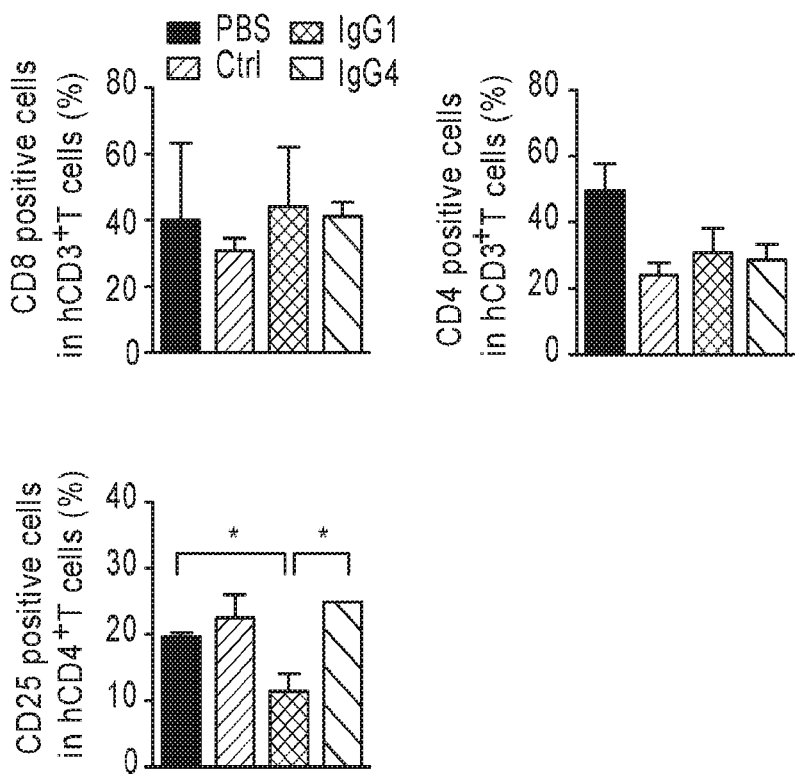
Figure 6:
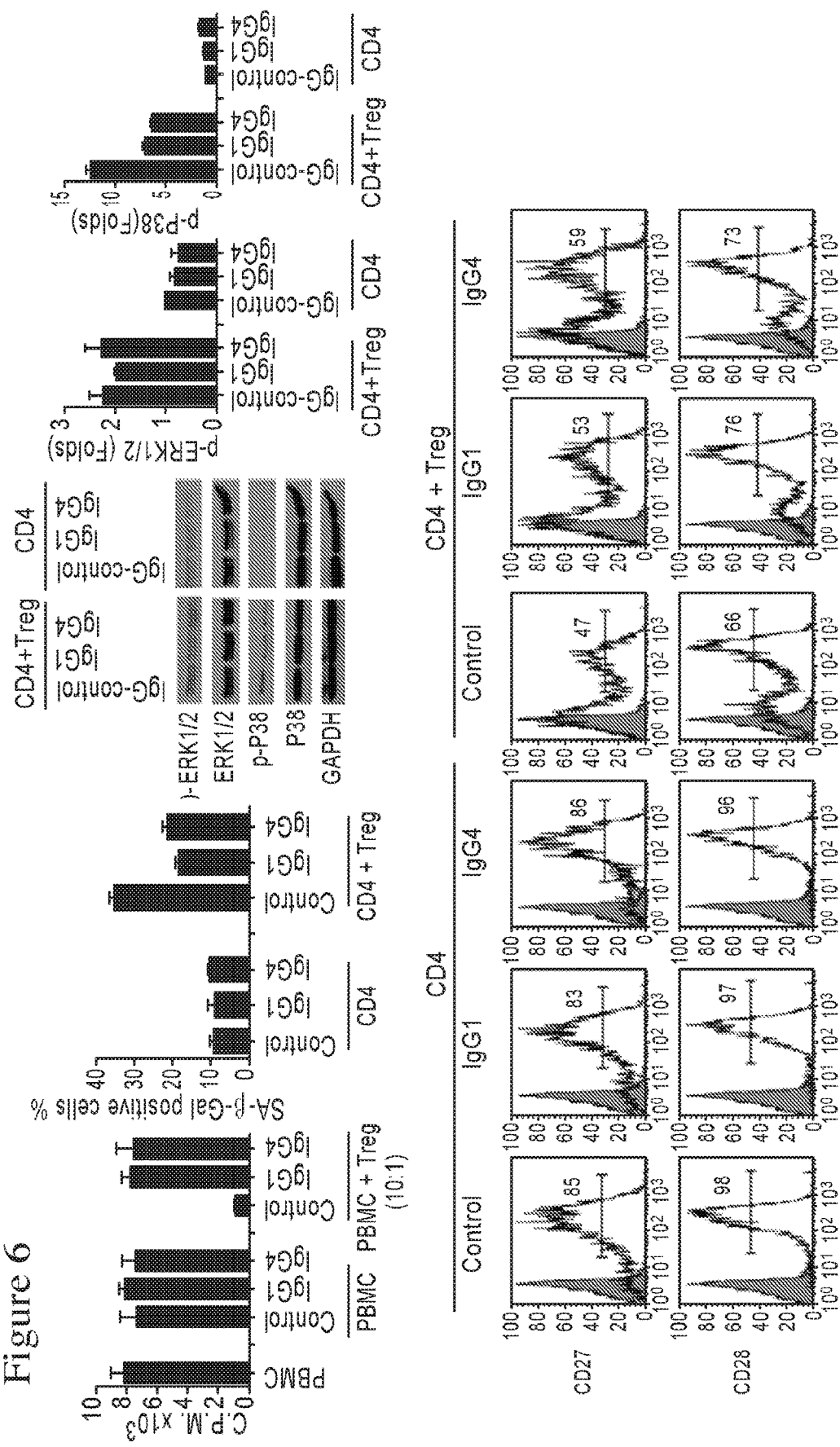
FIG. 6. Signaling inhibited by the humanized anti-CCR4 antibody. (A) Human PBMCs were incubated with or without Tregs in the presence and absence of control antibody, mAb2-3 IgG1, or mAb2-3 IgG4. PBMCs proliferation was detected by [3H] thymidine incorporation (CPM). (B) CD4+ T cells were isolated from human PBMCs and further incubated with Tregs in the presence and absence of control antibody, mAb2-3 IgG1, or mAb2-3 IgG4. Senescence-associated beta-galactosidase (SA-β-gal) positive cells were quantitated. (C) Western blotting conducted with anti-p-ERK1/2, ERK1/2, p-P38, and P38 antibodies and Western blot analyses; folds of p-ERK1/2 and p-P38 expression compared with the control IgG treated CD4+ T cells were determined. (D) The expression of CD27 and CD28 on CD4+ T cells were detected by flow cytometry after treated with control IgG, mAb2-3 IgG1, or mAb2-3 IgG4. All values are mean±S.D. These data revealed the additional function of mAb2-3 to inhibit Treg activity by reducing the expression of SA-β-gal and p-P38 and restoring the expression of CD27 and CD28, which provide co-stimulatory signals and are required for lymphocyte activation.

Immunocompromised mice received $5 \times 10^6$ IGROV-1 tumor cells, and tumors were allowed to grow until these reached an average of 50 mm$^3$. Subsequently, $1 \times 10^7$ IGROV-1 primed T-cells, $1 \times 10^6$ Treg cells, and either 1 mg/kg mAb2-3 IgG1, 1 mg/kg mAb2-3 IgG4, control IgG4 or PBS were injected via the tail vein. The antibodies were administered twice per week for a total of 35 days. The data from these experiments show that addition of either mAb2-3 IgG1 or mAb2-3 IgG4 resulted in a significant decrease in the size of the tumor compared to control IgG4 and PBS. (See FIG. 5A-B).

Example 7

Anti-CCR4 Antibodies on Proliferation of Teffs and the Abrogation of the Suppressive Function of Tregs Human PBMCs or CD4+ T cells were incubated with Tregs at 10:1 ratio with 20 µg/ml control IgG1, mAb2-3 IgG1, or mAb2-3 IgG4. The proliferation of human PBMCs and the transduced signals from CD4+ T cells were further detected by flow cytometry, western blot and staining. These data showed that the addition of either mAb2-3 IgG1 or mAb2-3 IgG4 resulted in the inhibition of Treg activity on suppression of human PBMCs, reduced the expression of SA-β-gal and p-P38, and restored the expression of CD27 and CD28, which provide co-stimulatory signals and are required for lymphocyte activation.

REFERENCES

1. Wood, K. J. & Sakaguchi, S. Regulatory T cells in transplantation tolerance. *Nat Rev Immunol* 3, 199-210 (2003).
2. Levings, M. K., Sangregorio, R. & Roncarolo, M. G. Human cd25(+)cd4(+) t regulatory cells suppress naive and memory T cell proliferation and can be expanded in vitro without loss of function. *J Exp Med* 193, 1295-1302 (2001).
3. Curiel, T. J., et al. Specific recruitment of regulatory T cells in ovarian carcinoma fosters immune privilege and predicts reduced survival. *Nat Med* 10, 942-949 (2004).
4. Iellem, A., et al. Unique chemotactic response profile and specific expression of chemokine receptors CCR4 and CCR8 by CD4(+)CD25(+) regulatory T cells. *J Exp Med* 194, 847-853 (2001).
5. Chang, D. K., et al. Humanization of an anti-CCR4 antibody that kills Cutaneous T Cell Lymphoma cells and abrogates suppression by T regulatory cells. *Mol Cancer Ther* (2012).
6. Han, T., et al. Human Anti-CCR4 Minibody Gene Transfer for the Treatment of Cutaneous T-Cell Lymphoma. *PLoS One* 7, e44455 (2012).
7. Imai, T., et al. Selective recruitment of CCR4-bearing Th2 cells toward antigen-presenting cells by the CC chemokines thymus and activation-regulated chemokine and macrophage-derived chemokine. *Int Immunol* 11, 81-88 (1999).
8. Wagsater, D., Dienus, O., Lofgren, S., Hugander, A. & Dimberg, J. Quantification of the chemokines CCL17 and CCL22 in human colorectal adenocarcinomas. *Mol Med Report* 1, 211-217 (2008).
9. Niens, M., et al. Serum chemokine levels in Hodgkin lymphoma patients: highly increased levels of CCL17 and CCL22. *Br J Haematol* 140, 527-536 (2008).
10. Jacobs, J. F., et al. Prognostic significance and mechanism of Treg infiltration in human brain tumors. *J Neuroimmunol* 225, 195-199 (2010).
11. Hiraoka, N., Onozato, K., Kosuge, T. & Hirohashi, S. Prevalence of FOXP3+ regulatory T cells increases during the progression of pancreatic ductal adenocarcinoma and its premalignant lesions. *Clin Cancer Res* 12, 5423-5434 (2006).
12. Woo, E. Y., et al. Regulatory CD4(+)CD25(+) T cells in tumors from patients with early-stage non-small cell lung cancer and late-stage ovarian cancer. *Cancer Res* 61, 4766-4772 (2001).
13. Zou, W. Regulatory T cells, tumour immunity and immunotherapy. *Nat Rev Immunol* 6, 295-307 (2006).
14. Yu, P., et al. Intratumor depletion of CD4+ cells unmasks tumor immunogenicity leading to the rejection of late-stage tumors. *J Exp Med* 201, 779-791 (2005).
15. Mahnke, K., et al. Depletion of CD4+CD25+ human regulatory T cells in vivo: kinetics of Treg depletion and alterations in immune functions in vivo and in vitro. *Int J Cancer* 120, 2723-2733 (2007).
16. Roncarolo, M. G. & Battaglia, M. Regulatory T-cell immunotherapy for tolerance to self antigens and alloantigens in humans. *Nat Rev Immunol* 7, 585-598 (2007).
17. Sakaguchi, S., Yamaguchi, T., Nomura, T. & Ono, M. Regulatory T cells and immune tolerance. *Cell* 133, 775-787 (2008).
18. Kohm, A.P., et al. Cutting Edge: Anti-CD25 monoclonal antibody injection results in the functional inactivation, not depletion, of CD4+CD25+ T regulatory cells. *J Immunol* 176, 3301-3305 (2006).
19. Baatar, D., et al. Human peripheral blood T regulatory cells (Tregs), functionally primed CCR4+ Tregs and unprimed CCR4− Tregs, regulate effector T cells using FasL. *J Immunol* 178, 4891-4900 (2007).
20. Mizukami, Y., et al. CCL17 and CCL22 chemokines within tumor microenvironment are related to accumulation of Foxp3+ regulatory T cells in gastric cancer. *Int J Cancer* 122, 2286-2293 (2008).
21. Gobert, M., et al. Regulatory T cells recruited through CCL22/CCR4 are selectively activated in lymphoid infiltrates surrounding primary breast tumors and lead to an adverse clinical outcome. *Cancer Res* 69, 2000-2009 (2009).
22. Faget, J., et al. Early detection of tumor cells by innate immune cells leads to T(reg) recruitment through CCL22 production by tumor cells. *Cancer Res* 71, 6143-6152 (2011).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated humanized monoclonal antibody that binds to the human CC chemokine receptor 4 (CCR4) and has an IgG4 heavy chain constant region, wherein the antibody comprises:
   a. a heavy chain with three CDRs comprising a CDR1 comprising amino acid sequence SEQ ID NO: 9, a CDR 2 comprising amino acid sequence SEQ ID NO:11, and a CDR 3 comprising amino acid sequence SEQ ID NO: 13; and
      a light chain with three CDRs comprising a CDR1 comprising amino acid sequence SEQ ID NO: 10, a CDR 2 comprising amino acid sequence SEQ ID NO: 12, and a CDR 3 comprising amino acid sequence SEQ ID NO: 14;
   b. a heavy chain with three CDRs comprising a CDR1 comprising amino acid sequence SEQ ID NO: 32, a CDR 2 comprising amino acid sequence SEQ ID NO: 11, and a CDR 3 comprising amino acid sequence SEQ ID NO: 34; and
      a light chain with three CDRs comprising a CDR1 comprising amino acid sequence SEQ ID NO: 10, a CDR 2 comprising amino acid sequence SEQ ID NO: 12, and a CDR 3 comprising amino acid sequence SEQ ID NO: 39;
   c. a heavy chain with three CDRs comprising a CDR1 comprising amino acid sequence SEQ ID NO: 33, a CDR 2 comprising amino acid sequence SEQ ID NO: 11, and a CDR 3 comprising amino acid sequence SEQ ID NO: 35; and
      a light chain with three CDRs comprising a CDR1 comprising amino acid sequence SEQ ID NO: 10, a CDR 2 comprising amino acid sequence SEQ ID NO: 12, and a CDR 3 comprising amino acid sequence SEQ ID NO: 40;
   d. a heavy chain with three CDRs comprising a CDR1 comprising amino acid sequence SEQ ID NO: 33, a CDR 2 comprising amino acid sequence SEQ ID NO: 11, and a CDR 3 comprising amino acid sequence SEQ ID NO: 36; and
      a light chain with three CDRs comprising a CDR1 comprising amino acid sequence SEQ ID NO: 10, a CDR 2 comprising amino acid sequence SEQ ID NO: 12, and a CDR 3 comprising amino acid sequence SEQ ID NO: 41;
   e. a heavy chain with three CDRs comprising a CDR1 comprising amino acid sequence SEQ ID NO: 33, a CDR 2 comprising amino acid sequence SEQ ID NO: 11, and a CDR 3 comprising amino acid sequence SEQ ID NO: 37; and
      a light chain with three CDRs comprising a CDR1 comprising amino acid sequence SEQ ID NO: 10, a CDR 2 comprising amino acid sequence SEQ ID NO: 12, and a CDR 3 comprising amino acid sequence SEQ ID NO: 42; or
   f. a heavy chain with three CDRs comprising a CDR1 comprising amino acid sequence SEQ ID NO: 31, a CDR 2 comprising amino acid sequence SEQ ID NO: 11, and a CDR 3 comprising amino acid sequence SEQ ID NO: 13; and
      a light chain with three CDRs comprising a CDR1 comprising amino acid sequence SEQ ID NO: 10, a CDR 2 comprising amino acid sequence SEQ ID NO: 12, and a CDR 3 comprising amino acid sequence SEQ ID NO: 38; and
      a heavy chain constant region comprising the amino acid sequence of SEQ ID NO: 6 or SEQ ID: 8, and wherein the antibody modulates regulatory T cell recruitment without inducing T lymphocyte depletion.

2. The antibody of claim 1, wherein the antibody comprises:
   a. a variable heavy chain region (VH) comprising the amino acid sequence of SEQ ID NO: 2 and a variable light chain region (VL) comprising the amino acid sequence of SEQ ID NO: 4;
   b. a variable heavy chain region (VH) comprising the amino acid sequence of SEQ ID NO: 16 and a variable light chain region (VL) comprising the amino acid sequence of SEQ ID NO: 18;
   c. a variable heavy chain region (VH) comprising the amino acid sequence of SEQ ID NO: 20 and a variable light chain region (VL) comprising the amino acid sequence of SEQ ID NO: 22;
   d. a variable heavy chain region (VH) comprising the amino acid sequence of SEQ ID NO: 24 and a variable light chain region (VL) comprising the amino acid sequence of SEQ ID NO: 26;
   e. a variable heavy chain region (VH) comprising the amino acid sequence of SEQ ID NO: 28 and a variable light chain region (VL) comprising the amino acid sequence of SEQ ID NO: 30; or
   f. a variable heavy chain region (VH) comprising the amino acid sequence of SEQ ID NO: 44 and a variable light chain region (VL) comprising the amino acid sequence of SEQ ID NO: 46.

3. The antibody of claim 2, wherein said antibody has a binding affinity of about 1.5 nm$^{-1}$ or less.

4. The antibody according to claim 1, wherein the antibody is linked to a therapeutic agent.

5. The antibody of claim 4, wherein said therapeutic agent is a toxin, a radiolabel, a siRNA, a small molecule, or a cytokine.

6. The antibody of claim 5 wherein said cytokine is IL-2 or TGF-beta.

7. A bi-specific antibody comprising the antibody of claim 1 and an antibody that immunospecifically binds to a second antigen.

8. The bi-specific antibody of claim 7, wherein the second antigen is a tumor associated antigen or a T-cell function modulating molecule.

9. The bi-specific antibody of claim 8, wherein the tumor associated antigen is CA-IX, ErbB2 or HVEM.

10. A cell producing the antibody of claim 1.

11. A method of inhibiting the migration of regulatory T-cells (Tregs) in a subject by administering to said subject the antibody of claim 1.

12. A method of claim 11, wherein lymphocytes are not depleted.

13. A method of claim 11, wherein effector T-cells are not depleted.

14. A method of claim 11, wherein Tregs are not depleted.

15. A method of augmenting an immune response to an antigen in a subject comprising administering to the subject the antibody of claim 1.

16. The method of claim 15, wherein said antigen is a viral antigen, a bacterial antigen or a tumor associated antigen.

17. The method of claim 15, wherein said administration of said antibody causes an increase in antigen specific T-cell activity.

18. The method of claim 15, wherein said administration of said antibody causes an increase in T-cell proliferation.

19. The method of claim 15, wherein effector T-cells are augmented.

20. A method of reversing regulatory T cell-mediated suppression of effector T cell proliferation comprising contacting a T cell with the antibody of claim 1.

21. A method of treating or alleviating a symptom of cancer, comprising administering to a subject in need thereof a composition comprising an antibody according to claim 1.

22. The method of claim 21, wherein said cancer is a solid cancer or a hematologic cancer.

23. The method of claim 22, wherein said hematologic cancer is cutaneous T-cell Lymphoma (CTCL), mycosis fungoides (MF), primary cutaneous anaplastic large cell Lymphoma (cutaneous ALCL), Sezary syndrome, or adult T cell Leukemia/Lymphoma (ATLL).

24. The method of claim 22, wherein the cancer is a solid cancer or a cancer that overexpresses CA IX, PD-LI, or HVEM.

25. The method of claim 22, were said solid cancer is renal cell carcinoma, breast cancer, lung cancer, ovarian cancer, prostate cancer, colon cancer, cervical cancer, brain cancer, liver cancer, pancreatic cancer, kidney or stomach cancer.

* * * * *